(12) United States Patent
Adamczyk et al.

(10) Patent No.: US 8,241,915 B2
(45) Date of Patent: *Aug. 14, 2012

(54) METHODS AND KITS FOR DETECTING HEMOGLOBIN IN TEST SAMPLES

(75) Inventors: Maciej Adamczyk, Gurnee, IL (US);
Roy J. Brashear, Mundelein, IL (US);
Phillip G. Mattingly, Third Lake, IL (US)

(73) Assignee: Abbott Laboratories, Abbott Park, IL (US)

( * ) Notice: Subject to any disclaimer, the term of this patent is extended or adjusted under 35 U.S.C. 154(b) by 465 days.

This patent is subject to a terminal disclaimer.

(21) Appl. No.: 12/362,331

(22) Filed: Jan. 29, 2009

(65) Prior Publication Data

US 2010/0178660 A1 Jul. 15, 2010

Related U.S. Application Data

(60) Provisional application No. 61/144,675, filed on Jan. 14, 2009.

(51) Int. Cl.
*G01N 33/72* (2006.01)
*G01N 33/48* (2006.01)

(52) U.S. Cl. ............................ 436/66; 356/40
(58) Field of Classification Search .................. None
See application file for complete search history.

(56) References Cited

U.S. PATENT DOCUMENTS

| | | | |
|---|---|---|---|
| 5,006,309 A | 4/1991 | Khalil et al. | |
| 5,063,081 A | 11/1991 | Cozzette et al. | |
| 5,089,424 A | 2/1992 | Khalil et al. | |
| 5,093,270 A * | 3/1992 | Chang et al. | 436/518 |
| 5,241,070 A | 8/1993 | Law | |
| 5,374,624 A | 12/1994 | Segel | |
| 5,468,646 A | 11/1995 | Mattingly et al. | |
| 5,543,524 A | 8/1996 | Mattingly et al. | |
| 5,783,699 A | 7/1998 | Mattingly et al. | |
| 6,316,265 B1 * | 11/2001 | Lee et al. | 436/67 |
| 6,602,679 B2 * | 8/2003 | Giri | 435/28 |
| 7,906,293 B2 * | 3/2011 | Mattingly et al. | 435/7.1 |
| 2003/0170881 A1 | 9/2003 | Davis et al. | |
| 2004/0018577 A1 | 1/2004 | Emerson Campbell et al. | |
| 2005/0054078 A1 | 3/2005 | Miller et al. | |
| 2005/0208670 A1 * | 9/2005 | Wittenberg et al. | 436/81 |
| 2006/0160164 A1 | 7/2006 | Miller et al. | |
| 2009/0263845 A1 | 10/2009 | Adamczyk et al. | |

FOREIGN PATENT DOCUMENTS

| WO | WO-9840750 A1 | 9/1998 |
|---|---|---|
| WO | WO-9854578 A1 | 12/1998 |
| WO | WO-2009026401 A1 | 2/2009 |

OTHER PUBLICATIONS

Adamczyk et al., Chemiluminescent acridinium-9-carboxamide boronic acid probes: Application to a homogeneous glycated hemoglobin assay, Bioorganic & Medicinal Chemistry Letters, 2006, vol. 16, 1324-1328.

Adamczyk et al., Linker-Medicated Modulation of the Cheiluminescent Signal From N10-(3-Sulfopropyl)-N-Sulfonylacridinium-9-carboxamide Tracers, Bioconjugate Chem. 2000, vol. 11, 714-724.

Adamczyk et al., Modulation of the Chemiluminescent Signal From N10-(3-Sulfopropyl)-N-Sulfonylacridinium-9-carboxamides. Tetrahedron, 1999, vol. 55, 10899-10914.

Adamczyk et al., Neopentyl 3-Triflyloxypropanesulfaonate Areactive Sulfopropylation Reagent for the Preparation of Chemiluminescent Labels, J Org Chem, 1998, vol. 63, 5636-5639.

Adamczyk et al., Regiodependent Luminescence Quenching of Biotinylated N-Sulfonyl-acridinium-9-carboxamides by Avidin. Organic Letters, 2003, 5 (21), 3779-3782.

Adamczyk et al., Synthesis of a Chemiluminescent Acridinium Hydroxylamine (AHA) for the Direct Detection of Abasic Sites in DNA, Organic Letters. 1999, 1 (5), 779-781.

Koch et al., Duration of red-cell storage and complications after cardiac surgery, N. Eng. J. Med., 2008, 358 (12), 1229-1239.

Lewis S. M. et al., Guidelines on Standard Operating Procedures for HAEMATOLOGY, Chapter 7—Haemoglobinometry, New Delhi; World Health Organization, 1999.

Lissi E. A. et al., Visible chemiluminescence associated with the reaction between methemoglobin or oxyhemoglobin with hydrogen peroxide, P. Photochem. Photobiol., 1994, 60 (5), 405-411.

Malinauskas R. A., Plasma hemoglobin measurement techniques for the in vitro evaluation of blood damage caused by medical devices, Artif. Organs, 1997, 21 (12), 1255-1267.

Mattingly et al., Chemiluminescent N-Sulfonylacridinium-9-Carboxamides and Their Application in Clinical Assays, Luminescence Biotechnology: Instruments and Applications (CRC Press: Boca Raton 2000), 2002. 77-105.

Mattingly Phillip G., Chemiluminescent 10-Methyl-Acridinium-9(N-Sulphonylcarboxamide) Salts. Synthesis and Kinetics of Light Emission, Journal of Bioluminescence and Chemiluminescence, 1991, vol. 6, 107-114.

McCapra, Chemiluminescence Involving Peroxide Decompositions, Photochemistry and Photobiology, 1965, vol. 4, 1111-1121.

Nohl H. et al., Chemiluminescence from activated heme compounds detected in the reaction of various xenobiotics with oxyhemoglobin: comparison with several heme/hydrogen peroxide systems, Free Radic Biol Med., 1993, 15 (3), 257-263.

Olsson T. et al., A sensitive method for determination of serum hemoglobin based on iso-luminol chemiluminescence, Clinica Chimica Acta, 1982, 122 (2), 125-133.

Razavi, Stable and versatile active acridinium esters I, Luminescence, 2000, vol. 15, 239-244.

Razavi, Stable and versatile active acridinium esters II, Luminescence, 2000, vol. 15, 245-249.

(Continued)

*Primary Examiner* — Rebecca Prouty
*Assistant Examiner* — Paul Martin
(74) *Attorney, Agent, or Firm* — Cheryl L. Becker

(57) ABSTRACT

The present invention relates to methods of detecting hemoglobin in a test sample. These methods can be used to diagnose a subject suffering from a genetic disorder relating to hemoglobin metabolism, to determine the eligibility of a subject to be a blood donor, to determine the age of a stored blood sample or to identify a hemolyzed plasma sample. The present invention also relates to kits for use in the above described methods.

30 Claims, 7 Drawing Sheets

OTHER PUBLICATIONS

Stratton L. P. et al., The reduction of methemoglobin levels by antioxidants, Hemoglobin, 1988, 12 (4), 353-368.

Tatsu Y. et al., Homogeneous chemiluminescent immunoassay based on complement-mediated mediated hemolysis of red blood cells, Anal Chem., 1990, 62 (19), 2103-2106.

Yoshiki Y. et al., Chemiluminescence of hemoglobin and identification of related compounds with the hemoglobin chemiluminescence in plasma, Photochem. Photobiol., 2001, 73 (5), 545-550.

PCT Notification of Transmittal of the International Search Report and the Written Opinion of the International Searching Authority, or the Declaration, for PCT Application No. PCT/US2010/020095, dated Jun. 9, 2010, 21 pages.

* cited by examiner

METHODS AND KITS FOR DETECTING HEMOGLOBIN IN TEST SAMPLES

RELATED APPLICATION INFORMATION

This application claims the benefit of U.S. application Ser. No. 61/144,675 filed on Jan. 14, 2009, the contents of which are herein incorporated by reference.

TECHNICAL FIELD

The present invention relates to methods of detecting and/or quantifying the amount of hemoglobin in a test sample. The methods of the present invention can be used to diagnose a subject suffering from a genetic disorder relating to hemoglobin metabolism, to determine the eligibility of a subject to be a blood donor, to determine the age of a stored blood sample and to identify a hemolyzed plasma sample. The present invention further relates to kits for use in the above described methods.

BACKGROUND

Adult hemoglobin A (HbA) is a tetrameric protein of molecular weight 64.5 kD, composed of 2 α-globins and 2 β-globins (α2β2). The alpha α-subunit is composed of 141 amino acids (See, SEQ ID NO: 1). The β-subunit is composed of 146 amino acids (See, SEQ ID NO:2). Both α and β-subunits are arranged in 8 helical segments (referred to as helix A-G). Each globin chain also contains a covalently bound heme molecule, composed of a porphyrin ring and an iron (Fe (II)) ligand located between helix E and F of the globin protein. Hemoglobin A constitutes approximately 97% of adult hemoglobin. Hemoglobin A2 is minor adult hemoglobin consisting of 2 α-globins and 2 δ-globins. The predominant fetal hemoglobin F consists of 2 α-globins and 2 γ-globins and is sometimes seen in neonates and adults.

Hemoglobin constitutes almost 90% of the dry weight of mature erythrocytes (e.g., red blood cells) and is responsible for the transport of oxygen and carbon dioxide between the lungs and body tissue. The heme-bound iron must be in the ferrous oxidation state, e.g., Fe(II), for hemoglobin to bind oxygen reversibly. Oxyhemoglobin can undergo autooxidation to methemoglobin (HbFe(III)) and higher oxidation states in the presence of other oxidants. In vivo, the methemoglobin concentration is less than 1.5% that of ferrous hemoglobin. Sometimes the intracellular mechanisms (e.g., cytochrome b5 methemoglobin reductase, glutathione, or nicotinamide adenine dinucleotide phosphate flavin reductase) fail to maintain hemoglobin in the ferrous state due to genetic abnormalities, or the presence of toxins or drugs, rendering the hemoglobin nonfunctional. Hemolytic anemia releases hemoglobin from erythrocytes where the free hemoglobin in circulation is subject to oxidative denaturation. Oxidation of hemoglobin has been problematic in the production and storage of hemoglobin-based blood substitutes.

Determination of hemoglobin concentration is an essential part of the blood donation process as an aid in eliminating harm to both anemic donors and potential transfusion recipients. Current standards require that donors have a minimum hemoglobin concentration of 12.5 g/dL (e.g., 0.0019 mol/L) corresponding to hematocrit of 38% or greater.

The determination of total hemoglobin concentration is also useful in assays reporting % hemoglobinA1c for monitoring blood glucose control.

The determination of hemoglobin in plasma is a sensitive measure of damage to the red blood cells during blood collection for clinical analysis, use of cardiovascular or hemodialysis medical devices, or during the processing of blood products (for example, packed red blood cells, plasma). Normally the concentration of hemoglobin in plasma is less than 10 mg/dL (1.6 μmol/L).

Methods for measuring the concentration of hemoglobin have been reviewed (See, Malinauskas, R. A. *Artif Organs*, 21, 1255-67 (1997)). Briefly, methods may be classified as direct optical techniques that measure the absorbance of undiluted oxyhemoglobin at a wavelength of 577 nm (e.g., Cripps, Kahn, Porter, Shinowara and first derivative methods); direct optical techniques that measure the absorbance of diluted hemoglobin at a wavelength of 415 nm (Harboe and Fairbanks All methods); and chemical methods such as Drabkin the method supported by international standards (See, Lewis S. M., Kumari S., Guidelines on Standard Operating Procedures for HAEMATOLOGY. Chapter 7—Haemoglobinometry. New Delhi: World Health Organization, 1999). The Drabkin method converts most forms of hemoglobin to cyanomethemoglobin (HiCN) by treatment with buffered potassium ferricyanide, $K_3Fe(CN)_6$ and potassium cyanide. To quantify the concentration fractions of hemoglobin, the absorbance at a wavelength of 540 nm is measured and compared to the International HiCN standard.

The method exemplified in the commercial MULTIGENT®Hemoglobin A1c Assay (Abbott Laboratories, List 02K96-20) converts digests hemoglobin with pepsin to give hematin which can be quantified at a wavelength of 604 nm.

Alternatively, assays for quantifying hemoglobin have been reported which are based on the use of hemoglobin to act as a catalyst for the oxidation of a chromogenic substrate in the presence of added hydrogen peroxide. Suitable substrates include for example, tetramethylbenzidene, o-toluidine, chlorpromazine, dianisidine and leucomalachite green (See, Malinauskas, R. A. *Artif Organs*, 21, 1255-67 (1997)). The absorbance of the oxidized substrate is proportional to the concentration of hemoglobin present.

Similarly, chemiluminescent assays for hemoglobin rely on the hemoglobin-catalyzed oxidation of luminol (See, Tatsu, Y.; Yoshikawa, S. *Anal Chem.*, 62, 2103-6 (1990)) or iso-luminol (Olsson, T.; Bergstrom, K.; Thore, A. *Clinica Chimica Acta*, 122:125 (1982)) in the presence of added hydrogen peroxide to generate a light signal proportional to the concentration of hemoglobin present.

Weak chemiluminescence has been reported from hemoglobin and methemoglogin upon reaction with hydrogen peroxide (See, Lissi, E. A.; Escobar, J.; Pascual, C.; del Castillo, M.; Schmitt, T. H.; Di Mascio, P. *Photochem. Photobiol.*, 60:405-11 (1994); Nohl, H.; Stolze, K. *Free Radic Biol Med.*, 15, 257-63 (1993)). The mechanism remains unresolved (See, Yoshiki, Y.; Iida, T.; Okubo, K.; Kanazawa, T. *Photochem. Photobiol.*, 73, 545-50 (2001)).

A chemiluminescent hemoglobin assay is described in WO 98/54578. Briefly, the hemoglobin content of a sample is determined by chemiluminescence based on the ability of hemoglobin to absorb radiation emitted by the chemiluminescent reaction of lucigenin and hydrogen peroxide. The concentration of hemoglobin is inversely related to the chemiluminescent signal.

A chemiluminescent assay for glycated hemoglobin fraction (See, Adamczyk, M.; Chen, Y.-Y.; Johnson, D. D.; Mattingly, P. G.; Moore, J. A.; Pan, Y.; Reddy, R. E. *Bioorg. Med. Chem. Lett.*, 16, 1324-8 (2006)) consisted of i) the conversion of all hemoglobin fractions to methemoglobin, ii) formation of an acridinium-9-carboxamide boronate/glycated hemoglobin complex, iii) initiating the chemiluminescent signal by the addition of excess hydrogen peroxide and base. The concentration of the glycated fraction of hemoglobin inversely related to the chemiluminescent signal.

There is a need in the art for new methods for determining the concentration of hemoglobin in test samples that do not employ toxic chemicals (such as potassium cyanide and potassium ferricyanide) and that exhibit improved sensitivity.

SUMMARY

In one aspect, the present invention relates to a method of detecting hemoglobin in a test sample. The method comprises the steps of:

a) adding at least one basic solution to a test sample;

b) adding an indicator solution to the test sample to generate a light signal, wherein the indicator solution comprises at least one acridinium compound, wherein steps a) and b) can be performed in any order; and c) measuring the light generated to detect the hemoglobin in the test sample.

In the above method, the test sample can be a non-biological forensic sample, stool, whole blood, serum, plasma, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil or a blood substitute.

In the above method, the basic solution is a solution having a pH of at least about 10.

In the above method, any acridinium compound can be used. For example, the acridinium compound can be an acridinium-9-carboxamide having a structure according to formula I:

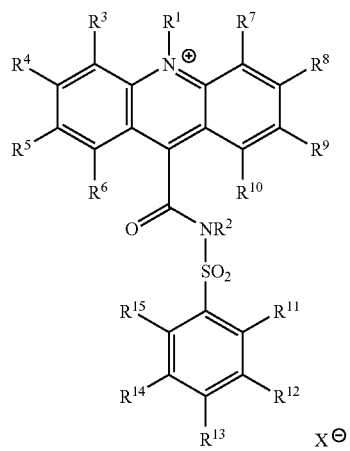

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

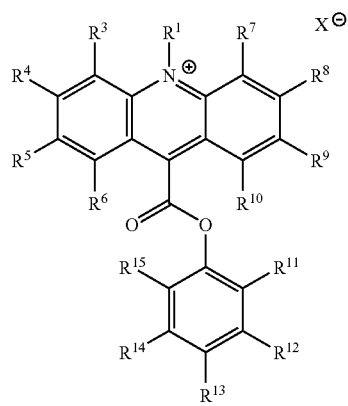

wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

In the above method, the indicator solution can further comprise at least one surfactant.

In the above method, the method can further comprise measuring the amount of hemoglobin in the test sample by relating the amount of light generated in the test sample by comparison to a standard curve for hemoglobin or to a reference standard. Optionally, the standard curve can be generated from solutions of hemoglobin of a known concentration.

In another aspect, the present invention relates to a method of detecting hemoglobin in a test sample. The method comprises the steps of:

a) adding at least one basic solution to a test sample; and b) measuring the current generated at at least one electrode to detect the hemoglobin in the test sample.

In the above method, the test sample is a non-biological forensic sample, stool, whole blood, serum, plasma, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil or a blood substitute.

In the above method, the basic solution is a solution having a pH of at least about 10.

In another aspect, the present invention relates to method of diagnosing a subject suffering from a genetic disorder relating to hemoglobin metabolism. The method comprises the steps of:

a) adding at least one basic solution to a test sample obtained from a subject suspected of suffering from a genetic disorder relating to hemoglobin metabolism;

b) adding an indicator solution to the test sample to generate a light signal, wherein the indicator solution comprises at least one acridinium compound, wherein steps a) and b) can be performed in any order;

c) quantifying the light generated to detect the hemoglobin in the test sample; and d) determining the concentration of hemoglobin in the test sample based on the amount of light quantified in step c); and e) comparing the concentration of hemoglobin in step (d) with a predetermined level, wherein if the concentration of hemoglobin determined in step (d) is lower or higher than the predetermined level, then a determination is made that the subject is suffering from a genetic disorder relating to hemoglobin metabolism.

In the above method, the test sample can be serum, plasma, whole blood, red blood cells and umbilical cord blood.

In the above method, the basic solution is a solution having a pH of at least about 10.

In the above method, any acridinium compound can be used. For example, the acridinium compound can be an acridinium-9-carboxamide having a structure according to formula I:

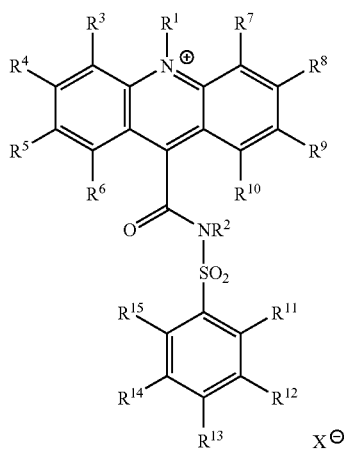

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

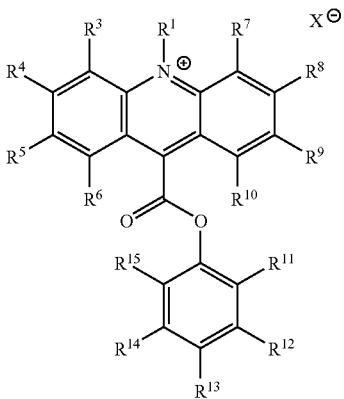

wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

In the above method, the indicator solution can further comprise at least one surfactant.

In the above method, the method can further comprise measuring the amount of hemoglobin in the test sample by relating the amount of light generated in the test sample by comparison to a standard curve for hemoglobin or to a reference standard. Optionally, the standard curve can be generated from solutions of hemoglobin of a known concentration.

In the above method, the genetic disorder relating to hemoglobin metabolism can be anemia or β-thalassemia.

In yet another aspect, the present invention relates to a method of determining the eligibility of a subject to be a blood donor. The method comprises the steps of:

a) adding at least one basic solution to a test sample obtained from a subject;

b) adding an indicator solution to the test sample to generate a light signal, wherein the indicator solution comprises at least one acridinium compound, wherein steps a) and b) can be performed in any order;

c) quantifying the light generated to detect the hemoglobin in the test sample;

d) determining the concentration of hemoglobin in the test sample based on the amount of light quantified in step c); and e) comparing the concentration of hemoglobin in step (d) with a predetermined level, wherein if the concentration of hemoglobin determined in step (d) is lower or higher than the predetermined level, then a determination is made that the subject is not eligible to be a blood donor.

In the above method, the test sample can be whole blood.

In the above method, the basic solution is a solution having a pH of at least about 10.

In the above method, any acridinium compound can be used. For example, the acridinium compound can be an acridinium-9-carboxamide having a structure according to formula I:

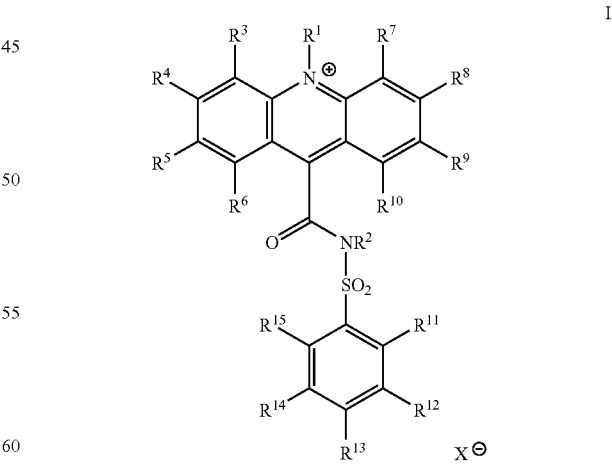

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

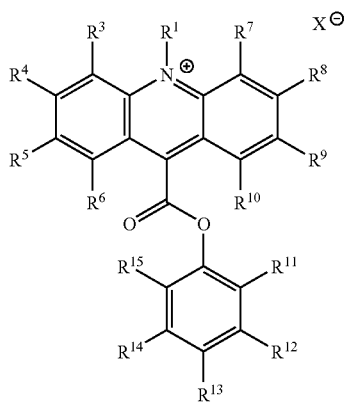

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

In the above method, the indicator solution can further comprise at least one surfactant.

In the above method, the method can further comprise measuring the amount of hemoglobin in the test sample by relating the amount of light generated in the test sample by comparison to a standard curve for hemoglobin or to a reference standard. Optionally, the standard curve can be generated from solutions of hemoglobin of a known concentration.

In still yet a further aspect, the present invention relates to a method of determining the age of a stored blood sample. The method comprises the steps of:

a) adding at least one basic solution to a blood sample;

b) adding an indicator solution to the blood sample to generate a light signal, wherein the indicator solution comprises at least one acridinium compound, wherein steps a) and b) can be performed in any order;

c) quantifying the light generated to detect the hemoglobin in the blood sample;

d) determining the concentration of hemoglobin in the blood sample based on the amount of light quantified in step c); and e) comparing the concentration of hemoglobin in step (d) with at least one predetermined level, wherein if the concentration of hemoglobin determined in step (d) is lower then the predetermined level, then the blood sample is determined to be an older blood sample.

In the above method, the blood sample is whole blood, red blood cells or umbilical cord blood.

In the above method, the basic solution is a solution having a pH of at least about 10.

In the above method, any acridinium compound can be used. For example, the acridinium compound can be an acridinium-9-carboxamide having a structure according to formula I:

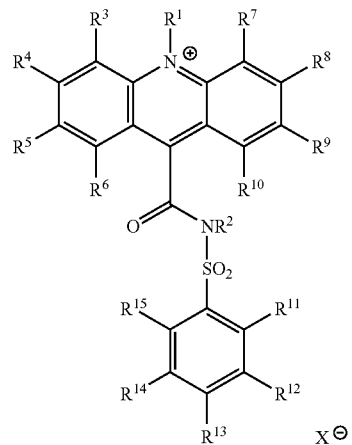

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

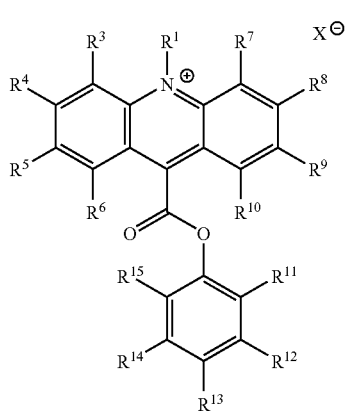

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

In the above method, the indicator solution can further comprise at least one surfactant.

In the above method, the method can further comprise measuring the amount of hemoglobin in the blood sample by relating the amount of light generated in the test sample by comparison to a standard curve for hemoglobin or to a reference standard. Optionally, the standard curve can be generated from solutions of hemoglobin of a known concentration.

In still yet a further aspect, the present invention relates to a method of identifying a hemolyzed serum or plasma sample. The method comprises the steps of:

a) adding at least one basic solution to a serum or plasma sample;

b) adding an indicator solution to the serum or plasma sample to generate a light signal, wherein the indicator solution comprises at least one acridinium compound, wherein steps a) and b) can be performed in any order;

c) quantifying the light generated to detect the hemoglobin in the serum or plasma sample;

d) determining the concentration of hemoglobin in the serum or plasma sample based on the amount of light quantified in step c); and e) comparing the concentration of hemoglobin in step (d) with a predetermined level, wherein if the concentration of hemoglobin determined in step (d) is higher then the predetermined level, then the serum or plasma sample is determined to be hemolyzed and further wherein if the concentration of hemoglobin determined in step (d) is lower then the predetermined level, then the serum or plasma sample is determined not to be hemolyzed.

In the above method, the basic solution is a solution having a pH of at least about 10.

In the above method, any acridinium compound can be used. For example, the acridinium compound can be an acridinium-9-carboxamide having a structure according to formula I:

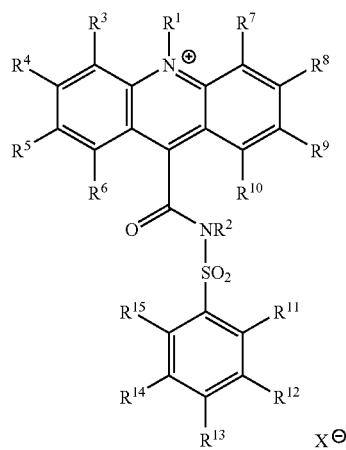

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\oplus}$ is an anion.

Alternatively, the acridinium compound is an acridinium-9-carboxylate aryl ester having a structure according to formula II:

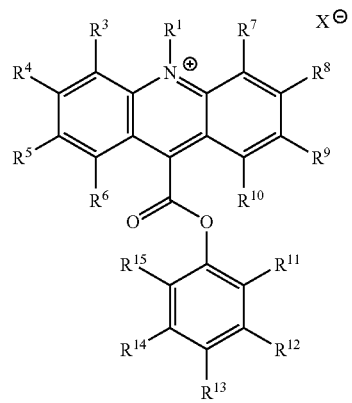

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\oplus}$ is an anion.

In the above method, the indicator solution can further comprise at least one surfactant.

In the above method, the method can further comprise measuring the amount of hemoglobin in the serum or plasma by relating the amount of light generated in the serum or plasma by comparison to a standard curve for hemoglobin or to a reference standard. Optionally, the standard curve can be generated from solutions of hemoglobin of a known concentration.

In still yet another aspect, the present invention relates to a kit for detecting hemoglobin in a test sample. The kit comprises:

a. at least one basic solution;

b. at least one indicator solution, wherein the indicator solution comprises at least one acridinium compound; and c. instructions for detecting hemoglobin in a test sample.

In the above kit, the basic solution is a solution having a pH of at least about 10.

In the above kit, any acridinium compound can be used. For example, the acridinium compound can be an acridinium-9-carboxamide having a structure according to formula I:

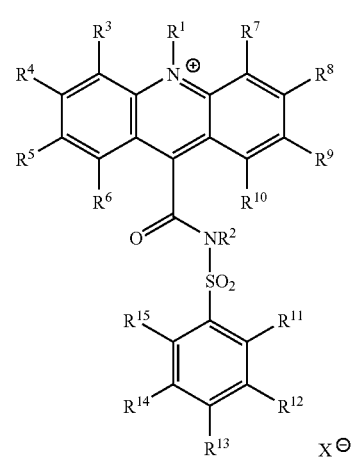

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

The indicator solution in the above kit can further comprise at least one surfactant.

In still yet another aspect, the present invention relates to a kit for detecting hemoglobin in a test sample. The kit comprises:

a. at least one basic solution;

b. at least one electrode; and c. instructions for detecting hemoglobin in a test sample.

In the above kit, the basic solution is a solution having a pH of at least about 10.

In still yet another aspect, the present invention relates to a kit for diagnosing a subject suffering from a genetic disorder relating to hemoglobin metabolism. The kit comprises:

a. at least one basic solution;

b. at least one indicator solution, wherein the indicator solution comprises at least one acridinium compound; and c. instructions for diagnosing a subject suffering from a genetic disorder relating to hemoglobin metabolism.

In the above kit, the basic solution is a solution having a pH of at least about 10.

In the above kit, any acridinium compound can be used. For example, the acridinium compound can be an acridinium-9-carboxamide having a structure according to formula I:

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

The indicator solution in the above kit can further comprise at least one surfactant.

In still yet another aspect, the present invention relates to a kit for determining the eligibility of a subject to be a blood donor. The kit comprises:

a. at least one basic solution;

b. at least one indicator solution, wherein the indicator solution comprises at least one acridinium compound; and c. instructions for determining the eligibility of a subject to be a blood donor.

In the above kit, the basic solution is a solution having a pH of at least about 10.

In the above kit, any acridinium compound can be used. For example, the acridinium compound can be an acridinium-9-carboxamide having a structure according to formula I:

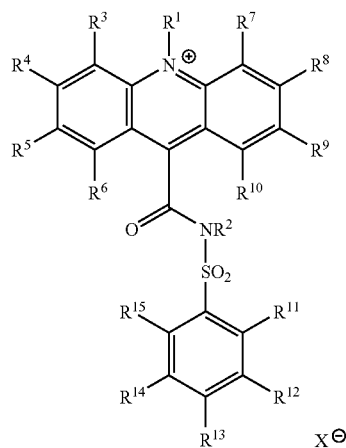

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

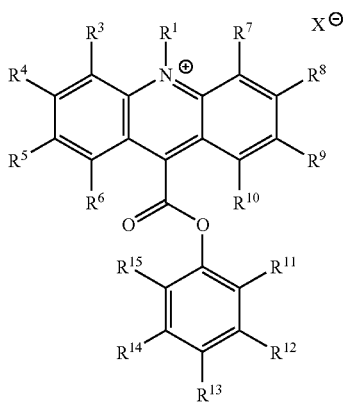

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

The indicator solution in the above kit can further comprise at least one surfactant.

In still yet another embodiment, the present invention relates to a kit for determining the age of a stored blood sample. The kit comprises:

a. at least one basic solution;

b. at least one indicator solution, wherein the indicator solution comprises at least one acridinium compound; and c. instructions for determining the age of a blood sample.

In the above kit, the basic solution is a solution having a pH of at least about 10.

In the above kit, any acridinium compound can be used. For example, the acridinium compound can be an acridinium-9-carboxamide having a structure according to formula I:

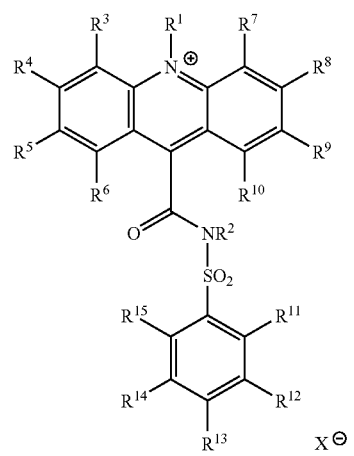

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

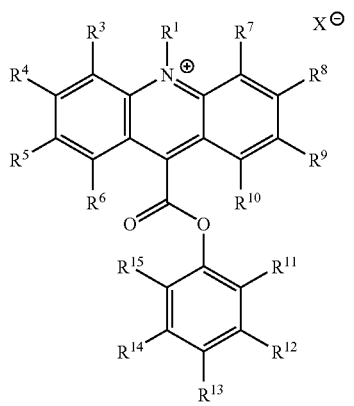

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

The indicator solution in the above kit can further comprise at least one surfactant.

In still yet another embodiment, the present invention relates to a kit for identifying a hemolyzed serum or plasma sample. The kit comprises:

a. at least one basic solution;

b. at least one indicator solution, wherein the indicator solution comprises at least one acridinium compound; and c. instructions for identifying a hemolyzed serum or plasma sample.

In the above kit, the basic solution is a solution having a pH of at least about 10.

In the above kit, any acridinium compound can be used. For example, the acridinium compound can be an acridinium-9-carboxamide having a structure according to formula I:

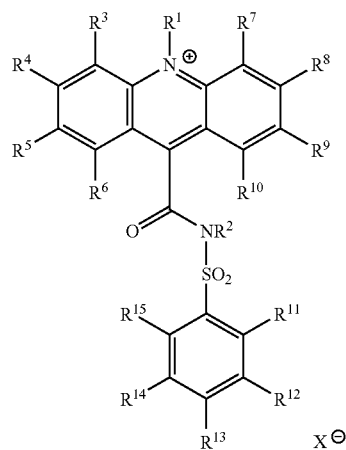

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Alternatively, the acridinium compound is an acridinium-9-carboxylate aryl ester having a structure according to formula II:

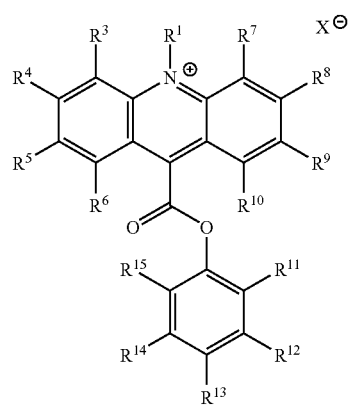

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

The indicator solution in the above kit can further comprise at least one surfactant.

DETAILED DESCRIPTION

Figure 1:
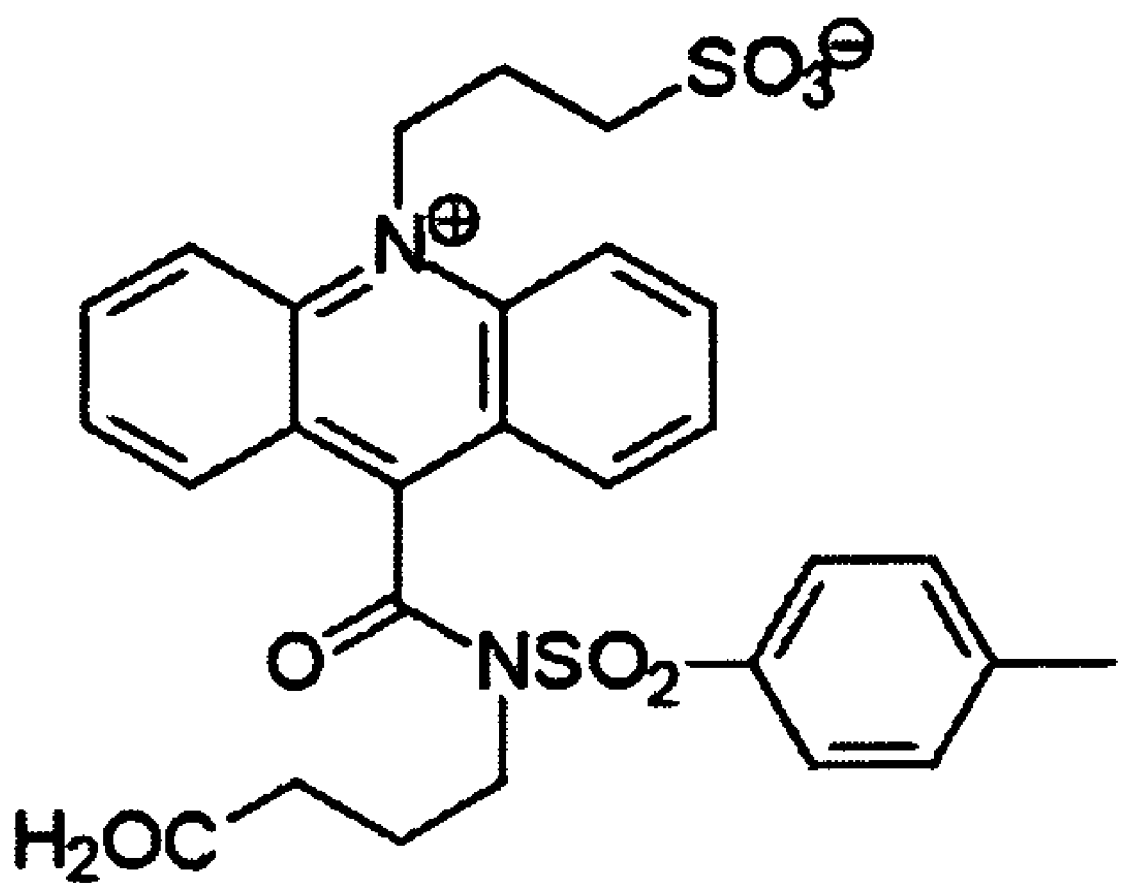
FIG. 1 shows the chemiluminescent detection reagent, 9-[[(3-Carboxypropyl)[(4-methylphenyl)sulfonyl]amino]-carbonyl]-10-(3-sulfopropyl)acridinium inner salt.

The present invention relates to methods of (a) detecting the presence of hemoglobin in a test sample; (b) quantifying the amount of hemoglobin in a test sample; (c) diagnosing a subject suffering from a genetic disorder relating to hemoglobin metabolism; (d) determining the eligibility of a subject to be a blood donor; (e) determining the age of a stored blood sample; and (f) identifying a hemolyzed plasma sample. The methods of the present invention do not employ toxic chemicals employed in the prior art and exhibit improved sensitivity compared to other methods known in the art. Further, the methods of the present invention can optionally employ very small test sample volumes and provide assay results rapidly (namely, from about 1 second to about 60 minutes), facilitating high-throughput automation. Additionally, the present invention relates to kits for performing each of the above methods.

A. DEFINITIONS

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Acyl (and Other Chemical Structural Group Definitions)

As used herein, the term "acyl" refers to a —C(O)$R_a$ group where $R_a$ is hydrogen, alkyl, cycloalkyl, cycloalkylalkyl, phenyl or phenylalkyl. Representative examples of acyl include, but are not limited to, formyl, acetyl, cylcohexylcarbonyl, cyclohexylmethylcarbonyl, benzoyl, benzylcarbonyl and the like.

As used herein, the term "alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

As used herein, the term "alkyl radical" means any of a series of univalent groups of the general formula $C_nH_{2n+1}$ derived from straight or branched chain hydrocarbons.

As used herein, the term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

As used herein, the term "amido" refers to an amino group attached to the parent molecular moiety through a carbonyl group (wherein the term "carbonyl group" refers to a —C(O)— group).

As used herein, the term "amino" means —$NR_bR_c$, wherein $R_b$ and $R_c$ are independently selected from the group consisting of hydrogen, alkyl and alkylcarbonyl.

As used herein, the term "aralkyl" means an aryl group appended to the parent molecular moiety through an alkyl group, as defined herein. Representative examples of aralkyl include, but are not limited to, benzyl, 2-phenylethyl, 3-phenylpropyl, and 2-naphth-2-ylethyl.

As used herein, the term "aryl" means a phenyl group, or a bicyclic or tricyclic fused ring system wherein one or more of the fused rings is a phenyl group. Bicyclic fused ring systems are exemplified by a phenyl group fused to a cycloalkenyl group, a cycloalkyl group, or another phenyl group. Tricyclic fused ring systems are exemplified by a bicyclic fused ring system fused to a cycloalkenyl group, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present disclosure can be optionally substituted with one-, two, three, four, or five substituents independently selected from the group consisting of alkoxy, alkyl, carboxyl, halo, and hydroxyl.

As used herein, the term "carboxy" or "carboxyl" refers to —$CO_2H$ or —$CO_2^-$.

As used herein, the term "carboxyalkyl" refers to a —$(CH_2)_nCO_2H$ or —$(CH_2)_nCO_2^-$ group where n is from 1 to 10.

As used herein, the term "cyano" means a —CN group.

As used herein, the term "cycloalkenyl" refers to a non-aromatic cyclic or bicyclic ring system having from three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Representative examples of cycloalkenyl groups include cyclohexenyl, octahydronaphthalenyl, norbornylenyl, and the like. The cycloalkenyl groups can be optionally substituted with one, two, three, four, or five substituents independently selected from the group consisting of alkoxy, alkyl, carboxyl, halo, and hydroxyl.

As used herein, the term "cycloalkyl" refers to a saturated monocyclic, bicyclic, or tricyclic hydrocarbon ring system having three to twelve carbon atoms. Representative examples of cycloalkyl groups include cyclopropyl, cyclopentyl, bicyclo[3.1.1]heptyl, adamantyl, and the like. The cycloalkyl groups of the present disclosure can be optionally substituted with one, two, three, four, or five substituents independently selected from the group consisting of alkoxy, alkyl, carboxyl, halo, and hydroxyl.

As used herein, the term "cycloalkylalkyl" means a —$R_dR_e$ group where $R_d$ is an alkylene group and $R_e$ is cycloalkyl group. A representative example of a cycloalkylalkyl group is cyclohexylmethyl and the like.

As used herein, the term "halogen" means a —Cl, —Br, —I or —F; the term "halide" means a binary compound, of which one part is a halogen atom and the other part is an element or radical that is less electronegative than the halogen, e.g., an alkyl radical.

As used herein, the term "hydroxyl" means an —OH group.

As used herein, the term "nitro" means a —$NO_2$ group.

As used herein, the term "oxoalkyl" refers to —$(CH_2)_nC(O)R_a$, where $R_a$ is hydrogen, alkyl, cycloalkyl, cycloalkylalkyl, phenyl or phenylalkyl and where n is from 1 to 10.

As used herein, the term "phenylalkyl" means an alkyl group which is substituted by a phenyl group.

As used herein, the term "sulfo" means a —$SO_3H$ group.

As used herein, the term "sulfoalkyl" refers to a —$(CH_2)_nSO_3H$ or —$(CH_2)_nSO_3^-$ group where n is from 1 to 10.

b) Anion

As used herein, the term "anion" refers to an anion of an inorganic or organic acid, such as, but not limited to, hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, aspartic acid, phosphate, trifluoromethansulfonic acid, trifluoroacetic acid and fluorosulfonic acid and any combinations thereof.

c) Pharmaceutical Composition

As used herein, the term "pharmaceutical composition" refers to any agent or drug, whether a small molecule (e.g., a drug containing an active agent, typically a non-peptidic) or biologic (e.g., a peptide or protein based drug, including any with modifications, such as, but not limited to PEGylation) that can be used to treat a subject suffering from a disease or condition that requires treatment.

d) Predetermined Level

As used herein, the term "predetermined level" refers generally at an assay cutoff value that is used to assess diagnostic results by comparing the assay results against the predetermined level, and where the predetermined level already that has been linked or associated with various clinical parameters (e.g., assessing risk, severity of disease, progression/nonprogression/improvement, determining the age of a test sample, determining whether a test sample (e.g., serum or plasma) has hemolyzed, etc.). The present invention provides exemplary predetermined levels, and describes the initial linkage or association of such levels with clinical parameters for exemplary assays as described herein. However, it is well known that cutoff values may vary dependent on the nature of the assay. It further is well within the ordinary skill of one in the art to adapt the invention herein for other assays to obtain assay-specific cutoff values for those other assays based on this description.

e) Specific Binding Partner

As used herein, the phrase "specific binding partner," as used herein, is a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal and complexes thereof, including those formed by recombinant DNA molecules.

f) Subject

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a human.

g) Test Sample

As used herein, the term "test sample" generally refers to a material being tested for and/or suspected of containing hemoglobin. For example, the material can be a non-biological forensic sample, such as clothing (e.g, shirts, pants, skirts, pajamas, socks, underwear, coats, gloves, hats, pantyhose, etc.), toothbrushes, combs, carpeting, towels, sheets, drapes, bedding, chairs, couches, seats from vehicles or boats, etc. Alternatively, the material may be a blood substitute. A number of blood substitutes are known in the art. Example of blood substitutes include, but are not limited to: recombinant human hemoglobin, crosslinked bovine polyhemoglobin (e.g., Hemopure, Biopure Corporation, Cambridge, Mass.) crosslinked human polyhemoglobin (e.g., PolyHeme®, Northfield Laboratories, Evanston, Ill.), polyethylene glycol-modified hemoglobin (e.g., Hemospan™, Sangart Inc., San Diego, Calif.), polymerized polynitroxyl hemoglobin (e.g., HemoZyme, SynZyme Technologies, LLC, Irvine, Calif.), perfluorocarbon based blood substitutes (See, U.S. Pat. No. 5,374,624; Oxycyte™, Costa Mesa, Calif.), etc. Alternatively, the material can be a biological material being tested for and/or suspected of containing hemoglobin. Biological materials may be derived from any biological source. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that hemoglobin remains in the test sample at a concentration proportional to that in an untreated test sample (e.g., namely, a test sample that is not subjected to any such pretreatment method(s)).

The methods of present invention can optionally employ small volumes of test samples. If such small volumes are employed, the volume of test samples employed is from about 0.001 μL to about 100 μL.

B. METHODS OF THE PRESENT INVENTION

In one aspect, the present invention involves a method of detecting and/or quantifying hemoglobin in a test sample. The method involves obtaining a test sample. The type and source of the test sample used in the method of the present invention is not critical. For example, the test sample can be a biological sample obtained from a subject. Alternatively, the test sample can be a non-biological sample obtained from any source or location, such as, but not limited to, a dwelling (e.g., house, apartment, trailer home, dorm room, hotel room, bungalow, etc), a school, a place of business, a car, a boat, motor home, bus, a park, etc.

Once the test sample is obtained, at least one basic solution (which serves as a trigger solution) and optionally, at least one indicator solution can each added to the test sample. The order in which the at least one basic solution and, optionally, the at least one indicator solution are added is not critical. The basic solution used in the method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the test sample depends on the concentration of the basic solution used in the assay. Based on the concentration of the basic solution used, one skilled in the art could easily determine the amount of basic solution to be used in the method described herein.

If an indicator solution is added to the test sample, the indicator solution comprises at least one acridinium compound. Preferably, the acridinium compound is an acridinium-9-carboxamide. Specifically, the acridinium-9-carboxamide has a structure according to formula I:

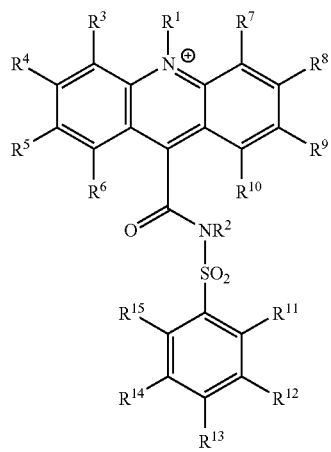

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^{\oplus}$ is an anion.

Methods for preparing acridinium 9-carboxamides are described in Mattingly, P. G. *J. Biolumin. Chemilumin.*, 6, 107-14; (1991); Adamczyk, M.; Chen, Y.-Y., Mattingly, P. G.; Pan, Y. *J. Org. Chem.*, 63, 5636-5639 (1998); Adamczyk, M.; Chen, Y.-Y.; Mattingly, P. G.; Moore, J. A.; Shreder, K. *Tetrahedron*, 55, 10899-10914 (1999); Adamczyk, M.; Mattingly, P. G.; Moore, J. A.; Pan, Y. *Org. Lett.*, 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.*, 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.*, 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\oplus}$ is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence*, 15:245-249 (2000); Razavi, Z et al., *Luminescence*, 15:239-244 (2000); and U.S. Pat. No. 5,241, 070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2, 3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, the test sample may be treated prior to addition of the at least one basic solution, the at least one indicator solution or prior to the addition of both the at least one basic solution and the at least one indicator solution. Such treatment may include dilution, ultrafiltration, extraction, precipitation, dialysis, chromatography and digestion. Such treatment may be in addition to and separate from any pretreatment that the test sample may receive or be subjected to as discussed previously herein. Moreover, if such treatment methods are employed with respect to the test sample, such treatment methods are such that hemoglobin remains in the test sample at a concentration proportional to that in an untreated test sample (e.g., namely, a test sample that is not subjected to any such treatment method(s)).

As mentioned briefly previously herein, the time and order in which the test sample, the at least one basic solution and optionally, the at least one indicator solution are added to form a mixture is not critical. Additionally, the mixture formed by the at least one basic solution, the at least one indicator solution or the at least one basic solution and at least one indicator solution, can optionally be allowed to incubate for a period of time. For example, mixture can be allowed to incubate for a period of time of from about 1 second to about 60 minutes. Specifically, the mixture can be allowed to incubate for a period of from about 1 second to about 18 minutes.

If at least one indicator solution is used and added to the test sample, after the addition of the at least one indicator solution and the at least one basic solution to the test sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

Thus, in the assays of the present invention when an indicator solution is used and added to the test sample, the chemiluminescent signal generated after the addition of the basic solution and the indicator solution indicates the presence of hemoglobin in the test sample which can be detected. The amount or concentration of hemoglobin in the test sample can be quantified based on the intensity of the signal generated. Specifically, the amount of hemoglobin contained in a test sample is proportional to the intensity of the signal generated. Specifically, the amount of hemoglobin present can be quantified based on comparing the amount of light generated to a standard curve for hemoglobin or by comparison to a reference standard. The standard curve can be generated using serial dilutions or solutions to hemoglobin of known concentration, by mass spectroscopy, gravimetrically and by other techniques known in the art.

Alternatively, if no indicator solution is used or added to the test sample, the presence of hemoglobin in the test sample can be detected using electrochemical detection, the techniques for which are well known to those skilled in the art. Such electrochemical detection often employs one or more electrodes connected to a device that measures and records an electrical current. Such techniques can be realized in a number of commercially available devices, such as the I-STAT® (Abbott Laboratories, Abbott Park, Ill.) system, which comprises a hand-held electrochemical detection instrument and self-contained assay-specific reagent cartridges. For example, in the present invention, the basic trigger solution could be contained in the self-contained hemoglobin reagent cartridge and upon addition of the test sample, a current would be generated at at least one electrode that is proportional to the amount of hemoglobin in the test sample.

The methods described herein can be used to identify the presence of hemoglobin, and hence blood, in a test sample. For example, the method described herein can be used to detect the presence of blood in test samples obtained by the police during the course of a criminal or missing persons investigation.

In another aspect, the present invention relates to methods of diagnosing subjects suffering from a genetic disorder relating to hemoglobin metabolism. The method involves obtaining a test sample from a subject. A subject from which a test sample can be obtained is any vertebrate. Preferably, the vertebrate is a mammal, especially a human. Examples of mammals include, but are not limited to, dogs, cats, rabbits, mice, rats, goats, sheep, cows, pigs, horses, non-human primates and humans. The subject may be suspected of suffering from a genetic disorder relating to hemoglobin metabolism. The test sample can be obtained from the subject using routine techniques known to those skilled in the art.

Once the test sample from a subject is obtained, at least one basic solution (which serves as a trigger solution) and at least one indicator solution are each added to the test sample. The order in which the at least one basic solution and the at least one indicator solution are added is not critical. The basic solution used in this method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the test sample depends on the concentration of the basic solution used in the assay. Based on the concentration of the basic solution used, one skilled in the art could easily determine the amount of basic solution to be used in the method described herein.

The indicator solution comprises at least one acridinium compound. Preferably, the acridinium compound is an acridinium-9-carboxamide. Specifically, the acridinium-9-carboxamide has a structure according to formula I:

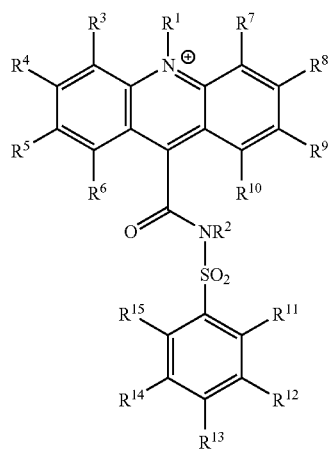

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\oplus$ is an anion.

As discussed previously herein, methods for preparing acridinium 9-carboxamides are described in Mattingly, P. G. *J. Biolumin. Chemilumin.,* 6, 107-14; (1991); Adamczyk, M.; Chen, Y.-Y., Mattingly, P. G.; Pan, Y. *J. Org. Chem.,* 63, 5636-5639 (1998); Adamczyk, M.; Chen, Y.-Y.; Mattingly, P. G.; Moore, J. A.; Shreder, K. *Tetrahedron,* 55, 10899-10914 (1999); Adamczyk, M.; Mattingly, P. G.; Moore, J. A.; Pan, Y. *Org. Lett.,* 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.,* 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.,* 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

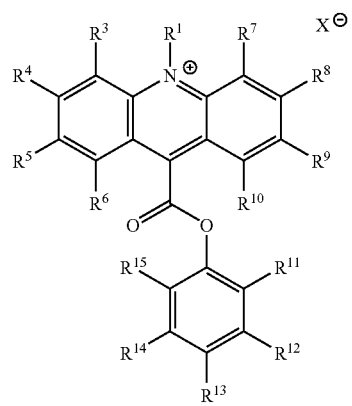

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.,* 4, 1111-21 (1965); Razavi, Z et al., *Luminescence,* 15:245-249 (2000); Razavi, Z et al., *Luminescence,* 15:239-244 (2000); and U.S. Pat. No. 5,241,070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (GENAPOL® C-100), isotridecanol polyglycol ether (GENAPOL® X-80), isotridecanol polyglycol ether (GENAPOL X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, the test sample may be treated prior to addition of the at least one basic solution, the at least one indicator solution or prior to the addition of both the at least one basic solution and the at least one indicator solution. Such treatment may include dilution, ultrafiltration, extraction, precipitation, dialysis, chromatography and digestion. Such treatment may be in addition to and separate from any pretreatment that the test sample may receive or be subjected to as discussed previously herein. Moreover, if such treatment methods are employed with respect to the test sample, such treatment methods are such that hemoglobin remains in the test sample at a concentration proportional to that in an untreated test sample (e.g., namely, a test sample that is not subjected to any such treatment method(s)).

As mentioned briefly previously herein, the time and order in which the test sample, the at least one basic solution and the at least one indicator solution are added to form a mixture is not critical. Additionally, the mixture formed by the at least one basic solution or the at least one indicator solution, can optionally be allowed to incubate for a period of time. For example, mixture can be allowed to incubate for a period of time of from about 1 second to about 60 minutes. Specifically, the mixture can be allowed to incubate for a period of from about 1 second to about 18 minutes.

After the addition of the at least one indicator solution and the at least one basic solution to the test sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

As discussed previously herein, the chemiluminescent signal generated after the addition of the basic solution and the indicator solution indicates the presence of hemoglobin in the test sample. The amount or concentration of hemoglobin in the test sample can then be quantified based on the intensity of the signal generated. Specifically, the amount of hemoglobin contained in a test sample is proportional to the intensity of the signal generated. Specifically, the amount or concentration of hemoglobin present can be quantified based on comparing the amount of light generated to a standard curve for hemoglobin or by comparison to a reference standard. The standard curve can be generated using serial dilutions or solutions to hemoglobin of known concentration, by mass spectroscopy, gravimetrically and by other techniques known in the art.

Once the amount or concentration of hemoglobin in the test sample is determined, the amount or concentration of hemoglobin determined in the test sample is compared with a predetermined level. Specifically, if the concentration of the hemoglobin determined in the test sample is lower or higher then the predetermined level (e.g., 7 to 8 g/dL), then a determination is made that the subject is suffering from a genetic disorder relating to hemoglobin metabolism. For example, if the concentration of hemoglobin in a test sample obtained from a subject is determined to be lower then a predetermined level, then the subject may be identified as suffering from a genetic disorder such as anemia or β-thalassemia. Once a determination is made that a subject is suffering from such a genetic disorder, the subject can be started on treatment with one or more pharmaceutical compositions.

In still yet another aspect, the present invention relates to a method of determining the eligibility of a subject to be a blood donor. The method involves obtaining a test sample from a subject. A subject from which a test sample can be obtained is any vertebrate. Preferably, the vertebrate is a mammal, especially a human. The test sample can be obtained from the subject using routine techniques known to those skilled in the art.

Once the test sample from a subject is obtained, at least one basic solution (which serves as a trigger solution) and at least one indicator solution are each added to the test sample. The order in which the at least one basic solution and the at least one indicator solution are added is not critical. The basic solution used in this method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the test sample depends on the concentration of the basic solution used in the assay. Based on the concentration of the basic solution used, one skilled in the art could easily determine the a I:

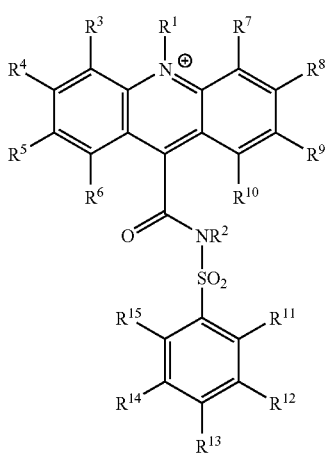

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\oplus$ is an anion.

As discussed previously herein, methods for preparing acridinium 9-carboxamides are described in Mattingly, P. G. *J. Biolumin. Chemilumin.*, 6, 107-14; (1991); Adamczyk, M.; Chen, Y.-Y., Mattingly, P. G.; Pan, Y. *J. Org. Chem.*, 63, 5636-5639 (1998); Adamczyk, M.; Chen, Y.-Y.; Mattingly, P. G.; Moore, J. A.; Shreder, K. *Tetrahedron*, 55, 10899-10914 (1999); Adamczyk, M.; Mattingly, P. G.; Moore, J. A.; Pan, Y. *Org. Lett.*, 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.*, 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.*, 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

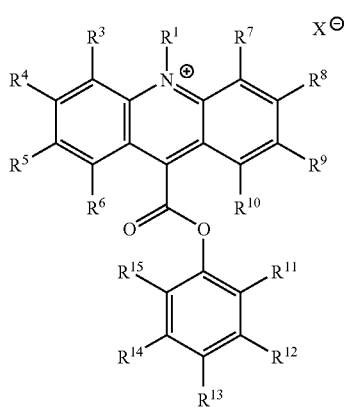

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence*, 15:245-249 (2000); Razavi, Z et al., *Luminescence*, 15:239-244 (2000); and U.S. Pat. No. 5,241,070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, the test sample may be treated prior to addition of the at least one basic solution, the at least one indicator solution or prior to the addition of both the at least one basic solution and the at least one indicator solution. Such treatment may include dilution, ultrafiltration, extraction, precipitation, dialysis, chromatography and digestion. Such treatment may be in addition to and separate from any pretreatment that the test sample may receive or be subjected to as discussed previously herein. Moreover, if such treatment methods are employed with respect to the test sample, such treatment methods are such that hemoglobin remains in the test sample at a concentration proportional to that in an untreated test sample (e.g., namely, a test sample that is not subjected to any such treatment method(s)).

As mentioned briefly previously herein, the time and order in which the test sample, the at least one basic solution and the at least one indicator solution are added to form a mixture is not critical. Additionally, the mixture formed by the at least one basic solution or the at least one indicator solution, can optionally be allowed to incubate for a period of time. For example, mixture can be allowed to incubate for a period of time of from about 1 second to about 60 minutes. Specifically, the mixture can be allowed to incubate for a period of from about 1 second to about 18 minutes.

After the addition of the at least one indicator solution and the at least one basic solution to the test sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

As discussed previously herein, the chemiluminescent signal generated after the addition of the basic solution and the indicator solution indicates the presence of hemoglobin in the test sample. The amount or concentration of hemoglobin in the test sample can then be quantified based on the intensity of the signal generated. Specifically, the amount of hemoglobin contained in a test sample is proportional to the intensity of the signal generated. Specifically, the amount or concentration of hemoglobin present can be quantified based on comparing the amount of light generated to a standard curve for hemoglobin or by comparison to a reference standard. The standard curve can be generated using serial dilutions or solutions to hemoglobin of known concentration, by mass spectroscopy, gravimetrically and by other techniques known in the art.

Once the amount or concentration of hemoglobin in the test sample is determined, the amount or concentration of hemoglobin determined in the test sample is compared with a predetermined level. Specifically, if the concentration of the hemoglobin determined in the test sample is lower or higher then the predetermined level (e.g., 12.5 grams/dL) then a determination is made that the subject is not eligible to a blood donor.

In still yet another aspect, the present invention relates to a method of determining the age of a stored blood sample based on the concentration of ferrous hemoglobin in the stored blood sample. Regulatory procedures have been established to define the shelf-life of donated blood and its components. Currently, RBC concentrates in CDPA-1 (citrate, dextrose, phosphate, and adenine) have a shelf-life of about 35 days at a temperature of from about 1 to about 6° C., while RBCs packed in an additive solution can be stored for about 42 days. These limitations are based on the 75% viability of the erythrocytes 24 hours after transfusion. Recent studies have indicated that these criteria may not be sufficient and that poor outcomes may result in patients transfused with RBCs older than 14 days (Koch et al., *N. Eng. J. Med.* 358: 1229-1239 (2008)). Some researchers have suggested that the increased risk of adverse outcomes is due to depletion of oxygen-carrying chemicals, i.e., hemoglobin. Methods for assessing the suitability of erythrocytes for transfusion by assessing the level of free choline in the erythrocytes, and a kit for use in such a method and use of the method or kit to screen potential blood donors and assess the suitability of processed blood products for transfusion prior to use has been disclosed in Adamczyk, et al, U.S. patent application Ser. No. 12/106,670, incorporated herein by reference.

The present method involves obtaining a test sample from a blood sample that has been stored for at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours at least 23 hours, at least 1 day, at least 2 days, at least 3 days, at least 4 days, at least 5 days, at least 6 days, at least 7 days, at least 14 days, at least 21 days, at least 30 days, at least 60 days, at least 90 days, at least 120 days, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, at least 24 months, at least 3 years, at least 4 years, at least 5 years, at least 6 years, at least 7 years, at least 8 years, at least 9 years, at least 10 years, etc. The stored blood sample can be whole blood, red blood cells (which can be buffered with glycerol), or umbilical cord blood. Techniques for storing blood samples is well known to those skilled in the art (e.g., a blood sample can be stored under refrigeration at a temperature of from about 1° C. to about 6° C., a blood sample can be frozen and stored at temperatures ranging from −18° C. to about −80° C., alternatively, a blood sample can be stored at room temperature). The stored blood sample can be obtained from any vertebrate. Preferably, the vertebrate is a mammal, especially a human. The stored blood sample can be obtained from any source, such as, but not limited to, a blood bank (e.g., a private or public blood bank) or a company providing umbilical blood storage services.

Once the test sample from a stored blood sample is obtained, at least one basic solution (which serves as a trigger solution) and at least one indicator solution are each added to the test sample. The order in which the at least one basic solution and the at least one indicator solution are added is not critical. The basic solution used in this method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the test sample depends on the concentration of the basic solution used in the assay. Based on the concentration of the basic solution used, one skilled in the art could easily determine the amount of basic solution to be used in the method described herein.

The indicator solution comprises at least one acridinium compound. Preferably, the acridinium compound is an acridinium-9-carboxamide. Specifically, the acridinium-9-carboxamide has a structure according to formula I:

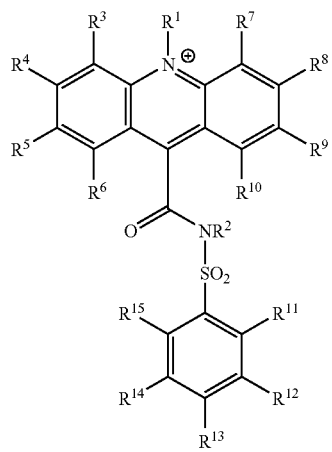

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\oplus$ is an anion.

As discussed previously herein, methods for preparing acridinium 9-carboxamides are described in Mattingly, P. G. *J. Biolumin. Chemilumin.,* 6, 107-14; (1991); Adamczyk, M.; Chen, Y.-Y., Mattingly, P. G.; Pan, Y. *J. Org. Chem.,* 63, 5636-5639 (1998); Adamczyk, M.; Chen, Y.-Y.; Mattingly, P. G.; Moore, J. A.; Shreder, K. *Tetrahedron,* 55, 10899-10914 (1999); Adamczyk, M.; Mattingly, P. G.; Moore, J. A.; Pan, Y. *Org. Lett.,* 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.,* 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.,* 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

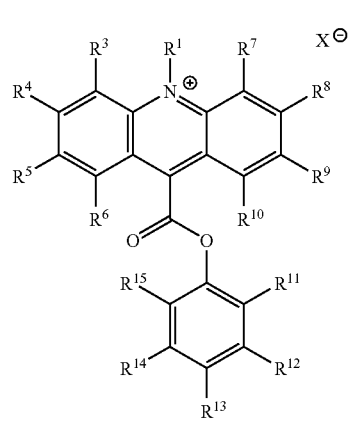

wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.,* 4, 1111-21 (1965); Razavi, Z et al., *Luminescence,* 15:245-249 (2000); Razavi, Z et al., *Luminescence,* 15:239-244 (2000); and U.S. Pat. No. 5,241, 070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2, 3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, the test sample may be treated prior to addition of the at least one basic solution, the at least one indicator solution or prior to the addition of both the at least one basic solution and the at least one indicator solution. Such treatment may include dilution, ultrafiltration, extraction, precipitation, dialysis, chromatography and digestion. Such treatment may be in addition to and separate from any pretreatment that the test sample may receive or be subjected to as discussed previously herein. Moreover, if such treatment methods are employed with respect to the test sample, such treatment methods are such that hemoglobin remains in the test sample at a concentration proportional to that in an untreated test sample (e.g., namely, a test sample that is not subjected to any such treatment method(s)).

As mentioned briefly previously herein, the time and order in which the test sample, the at least one basic solution and the at least one indicator solution are added to form a mixture is not critical. Additionally, the mixture formed by the at least one basic solution or the at least one indicator solution, can optionally be allowed to incubate for a period of time. For example, mixture can be allowed to incubate for a period of time of from about 1 second to about 60 minutes. Specifically, the mixture can be allowed to incubate for a period of from about 1 second to about 18 minutes.

After the addition of the at least one indicator solution and the at least one basic solution to the stored blood sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

As discussed previously herein, the chemiluminescent signal generated after the addition of the basic solution and the indicator solution indicates the presence of hemoglobin in the stored blood sample. The amount or concentration of hemoglobin in the stored blood sample can then be quantified based on the intensity of the signal generated. Specifically, the amount of hemoglobin contained in a stored blood sample is proportional to the intensity of the signal generated. Specifically, the amount or concentration of hemoglobin present can be quantified based on comparing the amount of light generated to a standard curve for hemoglobin or by comparison to a reference standard. The standard curve can be generated using serial dilutions or solutions to hemoglobin of known concentration, by mass spectroscopy, gravimetrically and by other techniques known in the art.

Once the amount or concentration of hemoglobin in the stored blood sample is determined, the amount or concentration of hemoglobin determined in the test sample is compared with a predetermined level. Specifically, if the concentration of the hemoglobin determined in the stored blood sample is lower then the predetermined level, then a determination is made that the stored blood sample is an older blood sample. Since the rate of hemoglobin degradation may be affected by the storage conditions of the sample, the predetermined level is preferably determined in the end-user setting. The steps to validate the predetermined level may include, the periodic measurement (for example, hourly, daily, weekly, monthly or yearly) of hemoglobin in one or more blood samples, or pooled blood samples, stored under conditions representative of the standard operating procedures used in the end-user setting, and over a set duration of time following the initial collection of the sample from the source subject and extending until the hemoglobin concentration has decreased by greater than about 50% or preferably about 75%, or more preferably, about 95%. The assignment of the predetermined level may be aided by plotting the periodic measurements of hemoglobin concentration versus time, and analyzing the resulting curve.

In still yet another aspect, the present invention further relates to a method of identifying a hemolyzed serum or plasma sample. Hemolysis is the breakage of the membrane of at least one red blood cell which cause the release of hemoglobin and other internal components into the surrounding fluid. Hemolysis is a common occurrence seen in serum and plasma samples and can compromise a laboratory's test parameters. In vitro hemolysis may be caused by improper specimen collection, specimen processing or specimen transport. Hemolysis may cause certain analytes to be increased due to leakage of red cell constituents or may cause interference in a test method.

The method of identifying a hemolyzed serum or plasma sample involves obtaining a serum or plasma sample. The serum or plasma sample may be a stored blood sample as described previously herein. The serum or plasma sample can be obtained is any vertebrate. Preferably, the vertebrate is a mammal, especially a human. The serum or plasma sample can be obtained using routine techniques known to those skilled in the art.

Once the serum or plasma sample is obtained, at least one basic solution (which serves as a trigger solution) and at least one indicator solution are each added to the serum or plasma sample. The order in which the at least one basic solution and the at least one indicator solution are added is not critical. The basic solution used in this method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the serum or plasma sample depends on the concentration of the basic solution used in the assay. Based on the concentration of the basic solution used, one skilled in the art could easily determine the amount of basic solution to be used in the method described herein.

The indicator solution comprises at least one acridinium compound. Preferably, the acridinium compound is an acridinium-9-carboxamide. Specifically, the acridinium-9-carboxamide has a structure according to formula I:

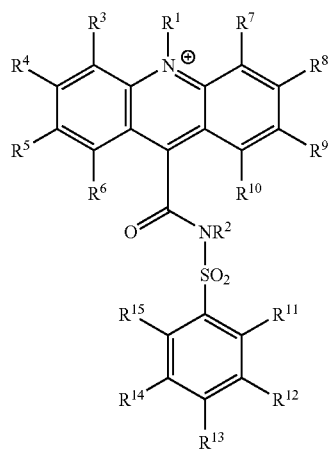

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\oplus$ is an anion.

As discussed previously herein, methods for preparing acridinium 9-carboxamides are described in Mattingly, P. G. *J. Biolumin. Chemilumin.*, 6, 107-14; (1991); Adamczyk, M.; Chen, Y.-Y., Mattingly, P. G.; Pan, Y. *J. Org. Chem.*, 63, 5636-5639 (1998); Adamczyk, M.; Chen, Y.-Y.; Mattingly, P. G.; Moore, J. A.; Shreder, K. *Tetrahedron*, 55, 10899-10914 (1999); Adamczyk, M.; Mattingly, P. G.; Moore, J. A.; Pan, Y. *Org. Lett.*, 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.*, 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.*, 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

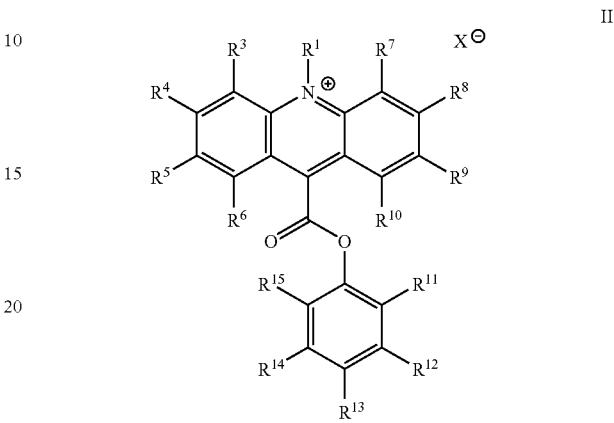

wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence,* 15:245-249 (2000); Razavi, Z et al., *Luminescence,* 15:239-244 (2000); and U.S. Pat. No. 5,241,070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, the serum or plasma sample may be treated prior to addition of the at least one basic solution, the at least one indicator solution or prior to the addition of both the at least one basic solution and the at least one indicator solution. Such treatment may include dilution, ultrafiltration, extraction, precipitation, dialysis, chromatography and digestion. Such treatment may be in addition to and separate from any pretreatment that the serum or plasma sample may receive or be subjected to as discussed previously herein. Moreover, if such treatment methods are employed with respect to the serum or plasma sample, such treatment methods are such that hemoglobin remains in the serum or plasma sample at a concentration proportional to that in an untreated serum or plasma sample (e.g., namely, a serum or plasma sample that is not subjected to any such treatment method(s)).

As mentioned briefly previously herein, the time and order in which the serum or plasma sample, the at least one basic solution and the at least one indicator solution are added to form a mixture is not critical. Additionally, the mixture formed by the at least one basic solution or the at least one indicator solution, can optionally be allowed to incubate for a period of time. For example, mixture can be allowed to incubate for a period of time of from about 1 second to about 60 minutes. Specifically, the mixture can be allowed to incubate for a period of from about 1 second to about 18 minutes.

After the addition of the at least one indicator solution and the at least one basic solution to the serum or plasma sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

As discussed previously herein, the chemiluminescent signal generated after the addition of the basic solution and the indicator solution indicates the presence of hemoglobin in the serum or plasma sample. The amount or concentration of hemoglobin in the serum or plasma sample can then be quantified based on the intensity of the signal generated. Specifically, the amount of hemoglobin contained in a serum or plasma sample is proportional to the intensity of the signal generated. Specifically, the amount or concentration of hemoglobin present can be quantified based on comparing the amount of light generated to a standard curve for hemoglobin or by comparison to a reference standard. The standard curve can be generated using serial dilutions or solutions to hemoglobin of known concentration, by mass spectroscopy, gravimetrically and by other techniques known in the art.

Once the amount or concentration of hemoglobin in the serum or plasma sample is determined, the amount or concentration of hemoglobin determined in the serum or plasma sample is compared with a predetermined level (e.g., 10 mg/dL). Specifically, if the concentration of the hemoglobin determined in the serum or plasma sample is lower then the predetermined level, then the serum or plasma sample is determined not to be hemolyzed. However, if the concentration of hemoglobin determined in the serum or plasma sample is the same as or higher the predetermined level, then the serum or plasma sample is determined to be hemolyzed. Serum or plasma samples determined to be hemolyzed pursuant to the method described herein are rejected and the sample is redrawn.

C. KITS

In another aspect, the present invention relates to a kit for detecting and/or quantifying the amount of hemoglobin in a test sample. The kit can contain at least one basic solution. The basic solution is a solution that contains at least one base and that has a pH greater than or equal to 10, preferably, greater than or equal to 12. Examples of basic solutions that can be included in the kit include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate.

Additionally, the kit can optionally contain at least one indicator solution containing at least one acridinium compound. The acridinium compound may comprise at least one acridinium-9-carboxamide, at least one acridinium-9-carboxylate aryl ester or any combinations thereof. More specifically, the acridinium-9-carboxamide that can be used has the structure according to Formula I:

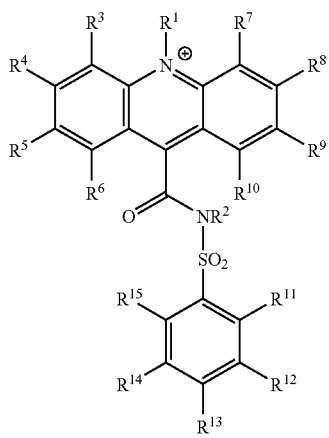

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\oplus$ is an anion.

Additionally, the acridinium-9-carboxylate aryl ester that can be used has a structure according to formula II:

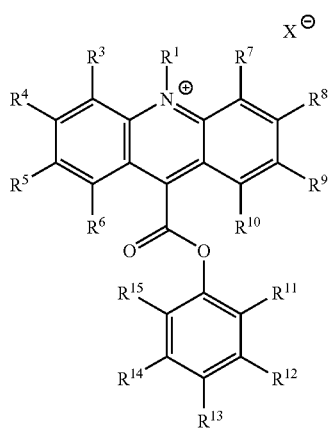

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

In addition, the at least one indicator solution can also contain at least one surfactant. Any surfactant that when dissolved in water, lowers the surface tension of the water and increases the solubility of organic compounds, can be included. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, if no indicator solution is included in the kit, the kit can comprise at least one electrode.

Also, the kit can also contain one or more instructions for detecting and/or quantifying the amount of hemoglobin in a test sample. The kit can also contain instructions for generating a standard curve for the purposes of quantifying the hemoglobin or a reference standard for purposes of quantifying the hemoglobin in the test sample. Such instructions optionally can be in printed form or on CD, DVD, or other format of recorded media.

In another embodiment, the present invention relates to a kit for diagnosing a subject suffering from a genetic disorder relating to hemoglobin metabolism. The kit can contain at least one basic solution. The basic solution is a solution that contains at least one base and that has a pH greater than or equal to 10, preferably, greater than or equal to 12. Examples of basic solutions that can be included in the kit include, but are not limited to, sodium hydroxide, potassium hydroxide, calcium hydroxide, ammonium hydroxide, magnesium hydroxide, sodium carbonat e and calcium bicarbonate.

Additionally, the kit can contain at least one indicator solution containing at least one acridinium compound. The acridinium compound may comprise at least one acridinium-9-carboxamide, at least one acridinium-9-carboxylate aryl ester or any combinations thereof. More specifically, the acridinium-9-carboxamide that can be used has the structure according to Formula I:

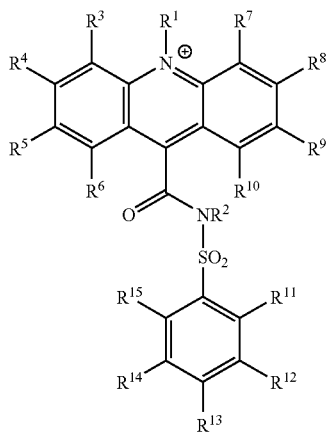

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\oplus$ is an anion.

Additionally, the acridinium-9-carboxylate aryl ester that can be used has a structure according to formula II:

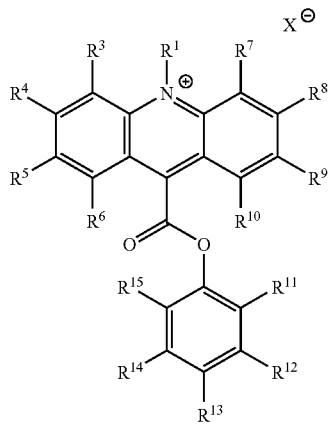

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

In addition to the at least one acridinium compound, the indicator solution can also contain at least one surfactant. Any surfactant that when dissolved in water, lowers the surface tension of the water and increases the solubility of organic compounds, can be used included. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-p-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-p-D-glucopyranoside, n-Dodecyl-p-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Also, the kit can also contain one or more instructions for diagnosing whether a subject is suffering from a genetic disorder. The kit can also contain instructions for generating a standard curve for the purposes of quantifying the hemoglobin or a reference standard for purposes of quantifying the hemoglobin in the test sample obtained from a subject. Such instructions optionally can be in printed form or on CD, DVD, or other format of recorded media.

In still yet another aspect, the present invention relates to a kit for determining the eligibility of a subject to be a blood donor. The kit can contain at least one basic solution. The basic solution is a solution that contains at least one base and that has a pH greater than or equal to 10, preferably, greater than or equal to 12. Examples of basic solutions that can be included in the kit include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate.

Additionally, the kit can contain at least one indicator solution containing at least one acridinium compound. The acridinium compound may comprise at least one acridinium-9-carboxamide, at least one acridinium-9-carboxylate aryl ester or any combinations thereof. More specifically, the acridinium-9-carboxamide that can be used has the structure according to Formula I:

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^{\oplus}$ is an anion.

Additionally, the acridinium-9-carboxylate aryl ester that can be used has a structure according to formula II:

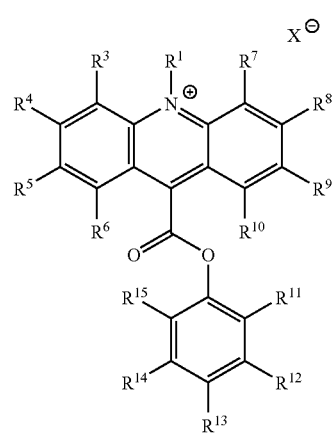

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\oplus}$ is an anion.

In addition to the at least one acridinium compound, the indicator solution can also contain at least one surfactant. Any surfactant that when dissolved in water, lowers the surface tension of the water and increases the solubility of organic compounds, can be included. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-p-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Also, the kit can also contain one or more instructions for determining the eligibility of a subject to be a blood donor. The kit can also contain instructions for generating a standard curve for the purposes of quantifying the hemoglobin or a reference standard for purposes of quantifying the hemoglobin in the test sample. Such instructions optionally can be in printed form or on CD, DVD, or other format of recorded media.

In still yet a further aspect, the present invention relates to a kit for determining the age of a stored blood sample (such as whole blood, serum, plasma, platelets, red blood cells or umbilical cord blood). The kit can contain at least one basic solution. The basic solution is a solution that contains at least one base and that has a pH greater than or equal to 10, preferably, greater than or equal to 12. Examples of basic solutions that can be included in the kit include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate.

Additionally, the kit can contain at least one indicator solution containing at least one acridinium compound. The acridinium compound may comprise at least one acridinium-9-carboxamide, at least one acridinium-9-carboxylate aryl ester or any combinations thereof. More specifically, the acridinium-9-carboxamide that can be used has the structure according to Formula I:

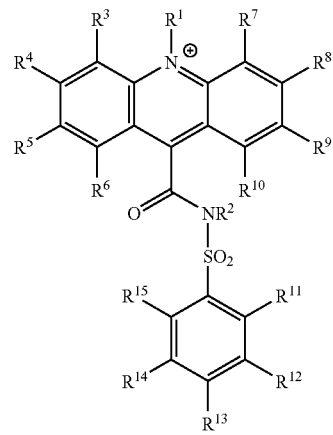

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\oplus$ is an anion.

Additionally, the acridinium-9-carboxylate aryl ester that can be used has a structure according to formula II:

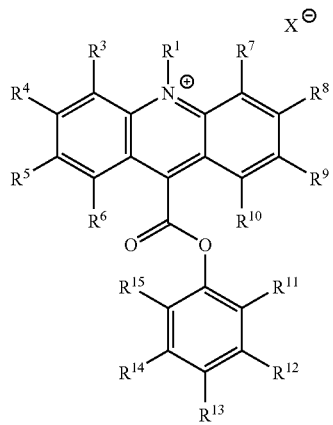

wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\oplus$ is an anion.

In addition to the at least one acridinium compound, the indicator solution can also contain at least one surfactant. Any surfactant that when dissolved in water, lowers the surface tension of the water and increases the solubility of organic compounds, can be included. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-p-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Also, the kit can also contain one or more instructions for determining the age of a stored blood sample. The kit can also contain instructions for generating a standard curve for the purposes of quantifying the hemoglobin or a reference standard for purposes of quantifying the hemoglobin in the stored blood sample. Such instructions optionally can be in printed form or on CD, DVD, or other format of recorded media.

In still yet a further aspect, the present invention relates to a kit for identifying a hemolyzed serum or plasma sample. The kit can contain at least one basic solution. The basic solution is a solution that contains at least one base and that has a pH greater than or equal to 10, preferably, greater than or equal to 12. Examples of basic solutions that can be included in the kit include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate.

Additionally, the kit can contain at least one indicator solution containing at least one acridinium compound. The acridinium compound may comprise at least one acridinium-9-carboxamide, at least one acridinium-9-carboxylate aryl ester or any combinations thereof. More specifically, the acridinium-9-carboxamide that can be used has the structure according to Formula I:

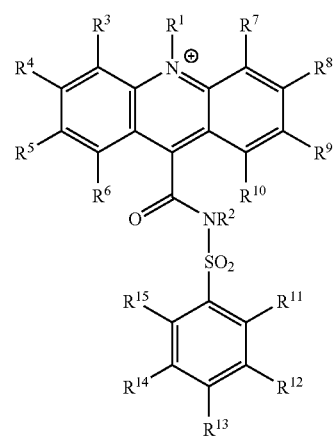

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^{\oplus}$ is an anion.

Additionally, the acridinium-9-carboxylate aryl ester that can be used has a structure according to formula II:

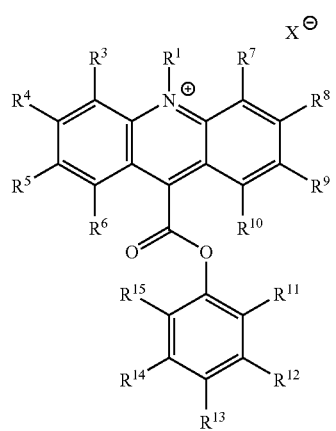

II wherein R¹ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\oplus}$ is an anion.

In addition to the at least one acridinium compound, the indicator solution can also contain at least one surfactant. Any surfactant that when dissolved in water, lowers the surface tension of the water and increases the solubility of organic compounds, can be included. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-p-D-maltoside, polyoxyethylene (10) dodecyl ether (GENAPOL® C-100), isotridecanol polyglycol ether (GENAPOL® X-80), isotridecanol polyglycol ether (GENAPOL® X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Also, the kit can also contain one or more instructions for identifying a hemolyzed serum or plasma sample. The kit can also contain instructions for generating a standard curve for the purposes of quantifying the hemoglobin or a reference standard for purposes of quantifying the hemoglobin in the serum or plasma sample. Such instructions optionally can be in printed form or on CD, DVD, or other format of recorded media.

D. ADAPTATIONS OF THE METHODS OF THE PRESENT INVENTION

The present invention as described herein also can be adapted for use in a variety of automated and semi-automated systems (including those wherein the solid phase comprises a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AXSYM®, IMX, PRISM, and Quantum II instruments, as well as other platforms. Moreover, the disclosure optionally is adaptable for the Abbott Laboratories commercial Point of Care (I-STAT®) electrochemical assay system for performing a variety of different types of assays (e.g., immunoassays, clinical chemistry assays, etc). Immunosensors, and their methods of manufacture and operation in single-use test devices are described, for example in, U.S. Pat. No. 5,063,081, U.S. Patent Application 2003/0170881, U.S. Patent Application 2004/0018577, U.S. Patent Application 2005/0054078, and U.S. Patent Application 2006/0160164, which are incorporated in their entireties by reference for their teachings regarding same.

In particular, with regard to the adaptation of the present assay to the I-STAT® system, the following example is provided. Other adaptations and configurations are well within the skill of those in the art. Specifically, a microfabricated silicon chip is manufactured with a pair of gold amperometric working electrodes and a silver-silver chloride reference electrode. This chip is assembled into an I-STAT® cartridge with a fluidics format suitable for the assay. Within the fluid pouch of the cartridge is an aqueous basic reagent.

In operation, a sample suspected of containing hemoglobin is added to the holding chamber of the hemoglobin test cartridge and the cartridge is inserted into the I-STAT® reader. A pump element within the cartridge forces the sample into a conduit containing the chip. Fluid is forced out of the pouch and into the conduit to mix with the sample. After applying the appropriate potential across the indicator electrode surface, with respect to a reference electrode, one or more electrochemical reactions takes place, all of which result in the consumption of the electroactive species generated upon reaction of hemoglobin and the basic aqueous reagent with the production of a measurable current. Based on the measured current, the reader is able to calculate the amount of hemoglobin in the sample by means of an embedded algorithm and factory-determined calibration curve.

It further goes without saying that the methods and kits as described herein necessarily encompass other reagents and methods for carrying out the assay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino) ethanesulfonic acid (MES), other salt, protein blockers, antimicrobial and surfactant. An exemplary calibrator diluent is ARCHITECT® Human calibrator diluent employed in certain kits (Abbott Laboratories, Abbott Park, Ill.), which comprises a buffer containing MES, other salt, a protein blocker and an antimicrobial.

By way of example, and not of limitation, examples of the present disclosures shall now be given.

Example 1

Detection of Hemoglobin in Whole Blood

Chemiluminescent Detection Reagent.
9-[[(3-Carboxypropyl)[(4-methylphenyl)sulfonyl]amino]-carbonyl]-10-(3-sulfopropyl)acridinium inner salt (See, FIG. 1 and Adamczyk, M.; Chen, Y.-Y., Mattingly, P. G.; Pan, Y. *J. Org. Chem.*, 63, 5636-5639 (1998)) was dissolved in reagent grade water containing sodium cholate (0.1% wt/vol) to give a concentration of 4 µM.

Whole Blood Dilutions.
A pooled whole blood sample (30 µL) was serially 2-fold diluted with buffer across the first row of a clear microplate to give 1:1, 2, 4, 8, 16, 32, 64, 128, 512, 1024, 2048 dilutions. By dilution 1:512 the solution was not visibly colored when viewed against a white background. These dilutions corresponded to nominal hemoglobin concentrations [Hb] of 2000, 1000, 500, 250, 125, 62.5, 31.25, 15.625, 7.8125, 3.90625, 1.953125, 0.9765625 µM.

Figure 2:
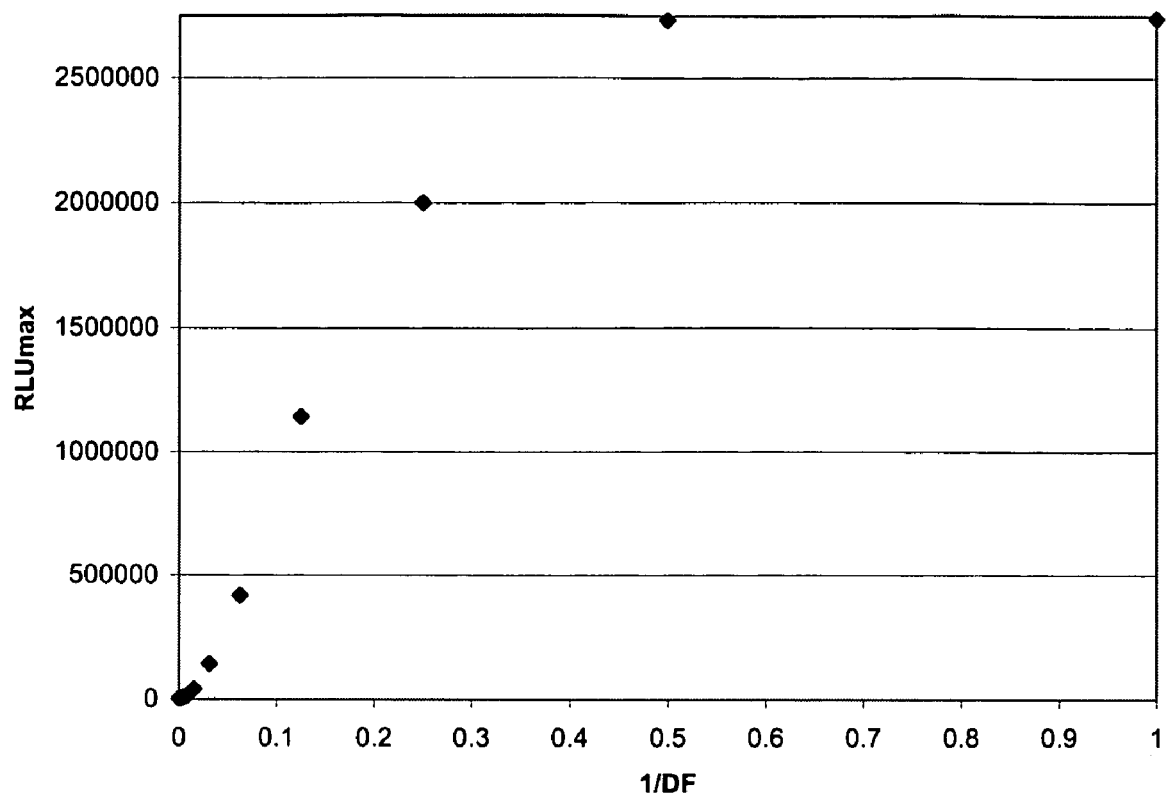
FIG. 2 shows the peak chemiluminescent signal (RLU-max) for each whole blood dilution listed in Table 1 for each reciprocal dilution factor (1/DF) as described in Example 1.
Figure 3:
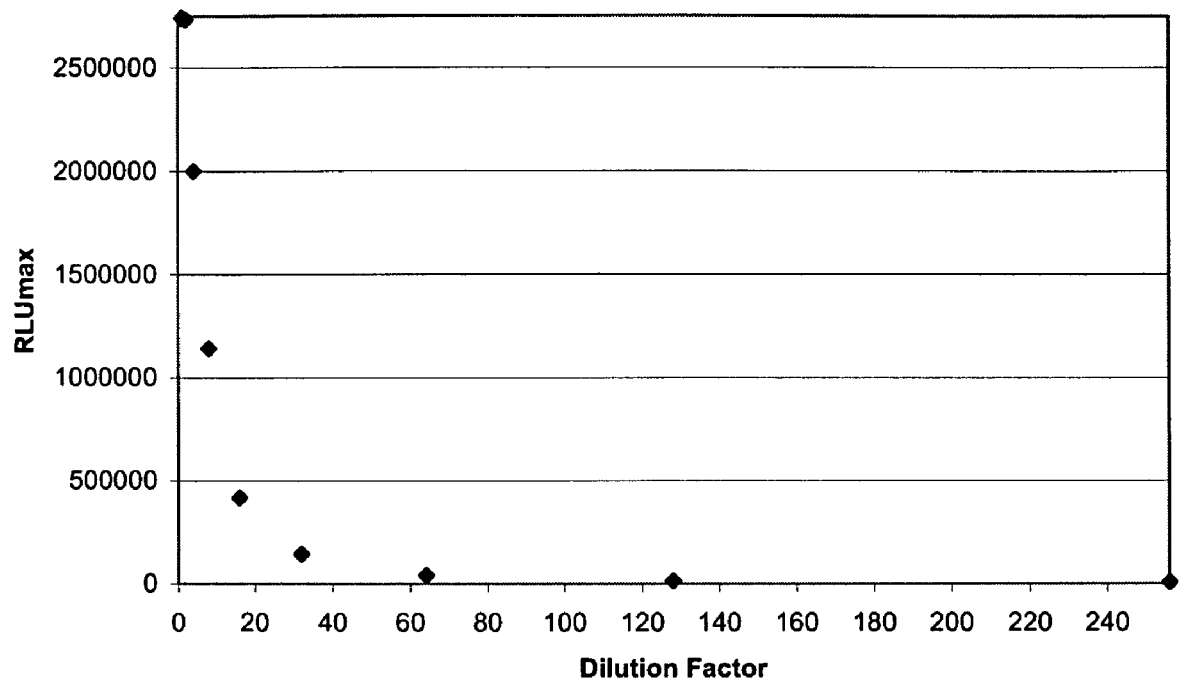
FIG. 3 shows the peak chemiluminescent signal RLUmax) for each whole blood dilution listed in Table 1 for each dilution factor (DF) as described in Example 1.
Figure 4:
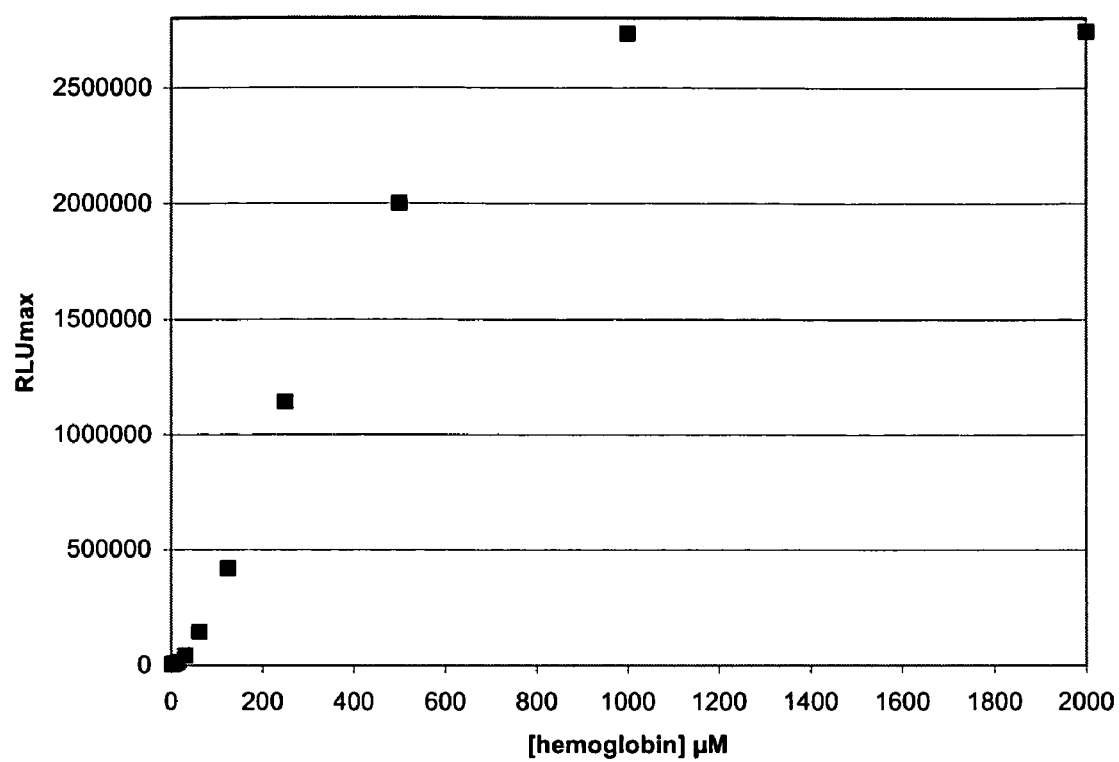
FIG. 4 shows the peak chemiluminescent signal (RLU-max) for each whole blood dilution listed in Table 1 for each nominal hemoglobin concentration (µM) as described in Example 1.

Assay Protocol.
The whole blood dilutions (1 µL) were arrayed in replicates of six in a 96-well microplate (Costar part no. 3972). The plate was loaded into a microplate luminometer (Mithras LB-940, Berthold Technologies U.S.A. LLC, Oak Ridge, Tenn.) at 28° C. Well by well, the chemiluminescent detection reagent (10 µL) and aqueous base (0.25 N sodium hydroxide, 30 µL, VWR part no. 3469-1) were sequentially added and the chemiluminescent signal (RLU, i.e, relative light units) recorded for 2 s. The peak chemiluminescent signal (RLUmax) for each whole blood dilution is listed below in Table 1 for each dilution factor (DF) and graphically in FIGS. 2 to 4.

TABLE 1

Detection of Hemoglobin in Whole Blood

| RLUmax | DF | 1/DF | [Hb] µM |
|---|---|---|---|
| 2742134 | 1 | 1 | 2000 |
| 2732867 | 2 | 0.5 | 1000 |
| 1999592 | 4 | 0.25 | 500 |
| 1141733 | 8 | 0.125 | 250 |
| 418842 | 16 | 0.0625 | 125 |
| 144405 | 32 | 0.03125 | 62.5 |
| 41587 | 64 | 0.015625 | 31.25 |
| 14193 | 128 | 0.0078125 | 15.625 |
| 6313 | 256 | 0.00390625 | 7.8125 |
| 3547 | 512 | 0.001953125 | 3.90625 |
| 3210 | 1024 | 0.000976563 | 1.953125 |
| 3183 | 2048 | 0.000488281 | 0.9765625 |

Example 2

Effect of Ultrafiltration of Hemoglobin Concentration

An aliquot of whole blood (100 µL) was filtered through a NANOSEP® 10K spin-filter (Pall Corporation, East Hills, N.Y., part no OD010C3J) using a TDx (Abbott Laboratories, Abbott Park, Ill.) microcentrifuge. The filtrate was colorless when viewed against a white background, indicating the removal of hemoglobin from the test sample.

The filtrate was analyzed by the assay protocol of Example 1. The resulting peak chemiluminescent signal (RLUmax) of 2493, indicated a residual hemoglobin concentration in the filtrate below 1 µM from the dose response curve generated in Example 1.

Example 3

Combined Effect of Aqueous Base Pretreatment and Ultrafiltration on Hemoglobin Analysis A whole blood sample (6 µL) was diluted with aqueous base (0.25 N sodium hydroxide, 180 µL, VWR part no. 3469-1) then filtered through a NANOSEP® 10K spin-filter (Pall Corporation, East Hills, N.Y., part no OD010C3J) using a TDx (Abbott Laboratories, Abbott Park, Ill.) microcentrifuge. The filtrate (31 µL) was arrayed in replicates of six (e.g. 6×31 µL) in a 96-well microplate (Costar part no. 3972). The plate was loaded into a microplate luminometer (Mithras LB-940, Berthold Technologies U.S.A. LLC, Oak Ridge, Tenn.) at 28° C. Well by well, the chemiluminescent detection reagent (10 µL) was added and the chemiluminescent signal (RLU, i.e, relative light units) recorded for 2 seconds. The peak chemiluminescent signal (RLUmax) was 40940.

Figure 5:
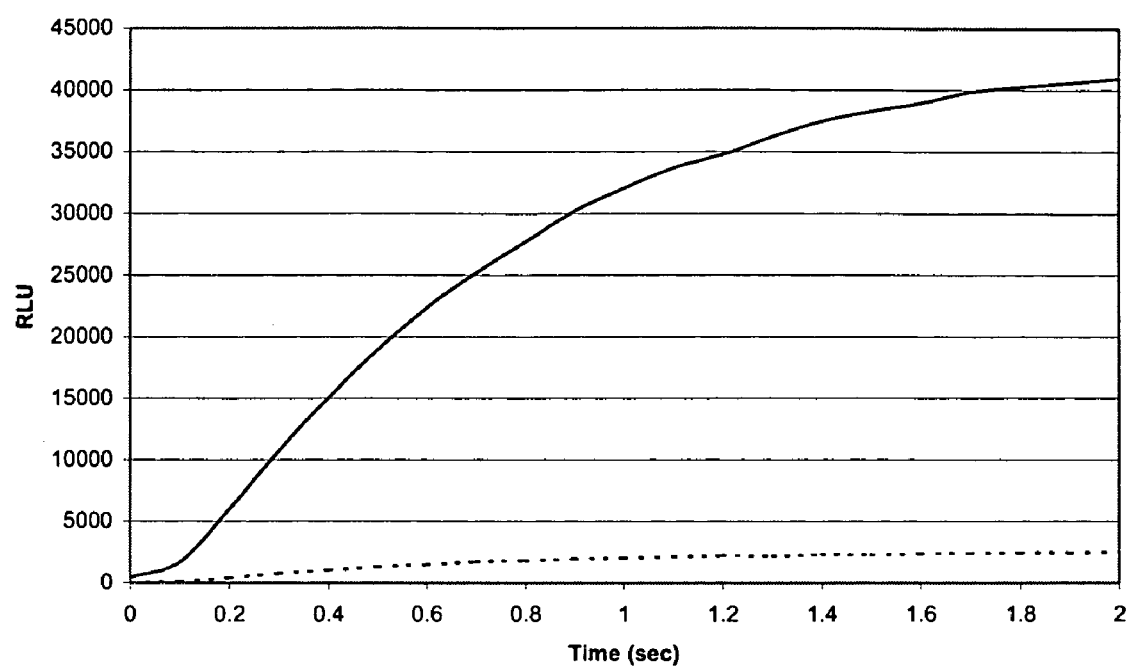
FIG. 5 shows a comparison of the chemiluminescent profile from whole blood samples treated with base before and after ultrafiltration as described in Example 3.

A comparison of the chemiluminescent profile from whole blood samples treated with base before (—Example 3) and after (- - - - Example 2) ultrafiltration is shown in FIG. 5.

This demonstrates, among other things, that the order of addition of the aqueous base and chemiluminescent detection reagent may be reversed in the detection of hemoglobin.

Example 4

Analysis of Fresh Whole Blood

Ferrous Hemoglobin Stock Solution.
Ferrous hemoglobin (mwt 64,500, Sigma Aldrich, St. Louis, Mo., part no. H-0267, <10% methemoglobin) was dissolved in phosphate buffer to give a 1 mM stock solution.

Ferrous Hemoglobin Standard Solutions.
The stock solution was diluted in phosphate buffer to give standard solutions of 100.00, 75.00, 50.00, 30.00, 20.00, 10.00, 5.00, 0.00 µM hemoglobin.

Figure 6:
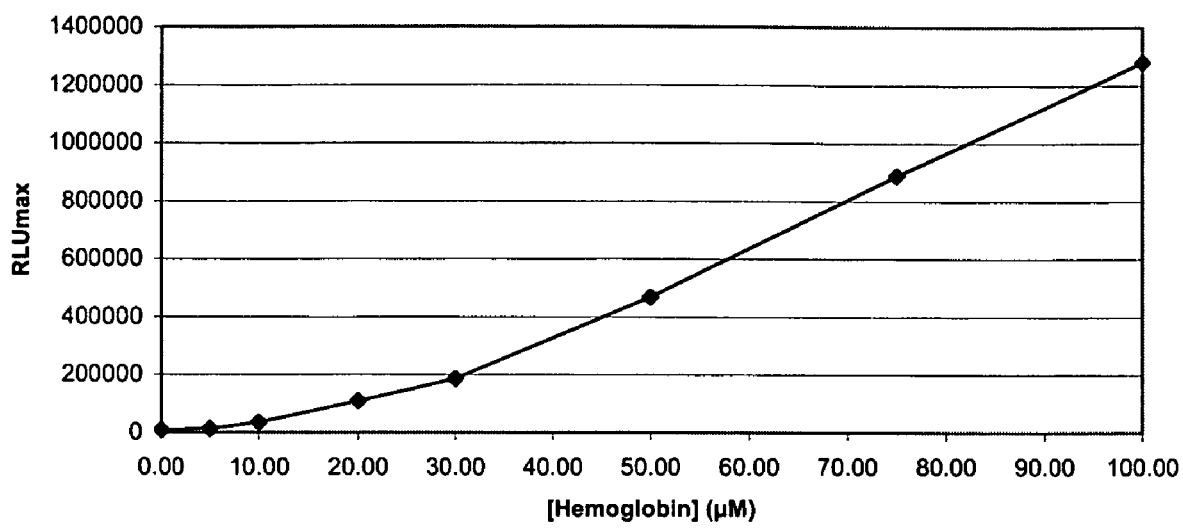
FIG. 6 shows the peak chemiluminescent signal (RLU-max) for each concentration of the ferrous hemoglobin standards listed in Table 2 as described in Example 4.
Figure 7:
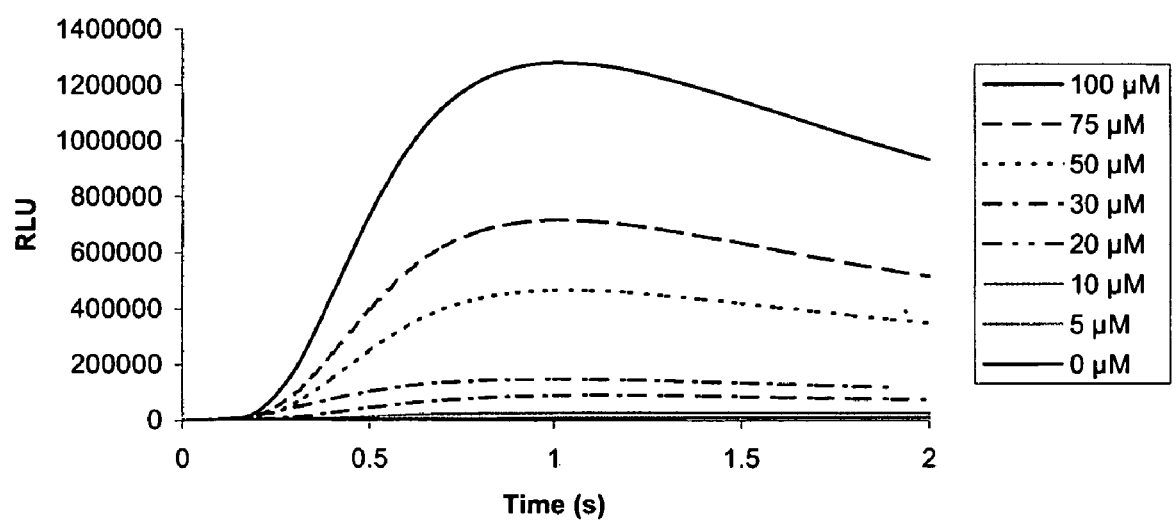
FIG. 7 shows the chemiluminescence profile (RLU vs time) for each ferrous hemoglobin standard concentration as described in Example 4.

Standard Dose-Response Curve.
The ferrous hemoglobin standards (1 µL) were arrayed in replicates of six in a 96-well microplate (Costar part no. 3972). The plate was loaded into a microplate luminometer (Mithras LB-940, Berthold Technologies U.S.A. LLC, Oak Ridge, Tenn.) at 28° C. Well by well, the chemiluminescent detection reagent (10 µL) and aqueous base (0.25 N sodium hydroxide, 30 µL, VWR part no. 3469-1) were sequentially added and the chemiluminescent signal (RLU, i.e, relative light units) recorded for 2 s. The peak chemiluminescent signal (RLUmax) for standard dilution are listed in Table 2 and graphically in FIG. 6. The chemiluminescence profile (RLU vs time) for each standard concentration is shown in FIG. 7.

Fresh Whole Blood Assay.
Fresh whole blood collected by finger stick was rapidly lysed by freeze/thaw (dry ice/acetone, −78 C, 3×), then an aliquot was diluted 1:50 in phosphate buffer. The diluted test sample (1 µL) was arrayed in replicates of six in a 96-well microplate (Costar part no. 3972). The plate was loaded into a microplate luminometer (Mithras LB-940, Berthold Technologies U.S.A. LLC, Oak Ridge, Tenn.) at 28° C. Well by well, the chemiluminescent detection reagent (10 μL) and aqueous base (0.25 N sodium hydroxide, 30 μL, VWR part no. 3469-1) were sequentially added and the chemiluminescent signal (RLU, i.e, relative light units) recorded for 2 seconds.

The peak chemiluminescent signal (RLUmax) was 565322, which corresponded to a hemoglobin concentration of 2.77 mM in the undiluted fresh whole blood sample.

TABLE 2

| Concentration | RLUmax |
|---|---|
| 100.00 | 1280088 |
| 75.00 | 888918 |
| 50.00 | 468027 |
| 30.00 | 186545 |
| 20.00 | 110975 |
| 10.00 | 36548 |
| 5.00 | 14685 |
| 0.00 | 9480 |

Example 5

Effect of Sample Age on Hemoglobin Concentration

The blood sample of Example 4 was stored overnight at −20° C., and then re-analyzed using the same protocol as Example 4 the next day. The recorded peak chemiluminescent signal (RLUmax) was 391470 corresponding to a hemoglobin concentration of 2.23 mM, thus showing a decrease in the hemoglobin concentration in the stored blood sample of 0.54 mM (19.5%).

A lysed whole blood sample that had been stored for greater than one year, was analyzed using the same protocol as Example 4. The recorded peak chemiluminescent signal (RLUmax) was 77892, corresponding to a hemoglobin concentration of 0.75 mM.

This would indicate that hemoglobin concentration in this sample decreased about 70% from that expected in a freshly collected sample. This is consistent with what has been reported for samples stored for a year or more under similar conditions (See, Stratton, L. P.; Rudolph, A. S.; Knoll, W. K., Jr.; Bayne, S.; Farmer, M. C. *Hemoglobin*, 12:353 (1988)).

One skilled in the art would readily appreciate that the present disclosure is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of detecting hemoglobin in a test sample, the method consisting essentially of the steps of:
    a) adding at least one basic solution to a test sample;
    b) adding an indicator solution to the test sample to generate a light signal,
    wherein the indicator solution comprises at least one acridinium compound, wherein steps a) and b) can be performed in any order; and
    c) measuring the increase in light generated to detect the hemoglobin in the test sample, wherein the light generated is proportional to the amount of hemoglobin in the test sample; and wherein the at least one acridinium compound comprises an acridinium-9-carboxamide or an acridinium-9-carboxylate aryl ester,
    wherein the acridiniurn-9-carboxamide has a structure according to formula I:

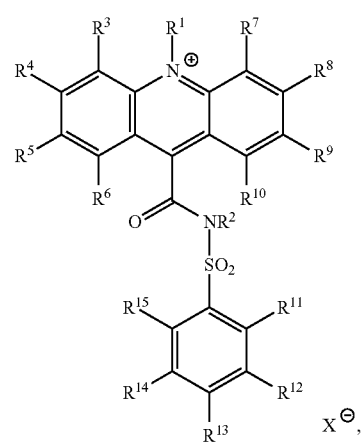

wherein $R^1$ and $R^2$ are each independently selected from the group consisting of: alkyl, alkenyl, alkynyl, aryl or aralkyl, sutfoalkyl, carboxyalkyl and oxoalkyl, and;

wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present, $X^\ominus$ is an anion, and wherein acridinium-9-carboxylate aryl ester has a structure according to formula II:

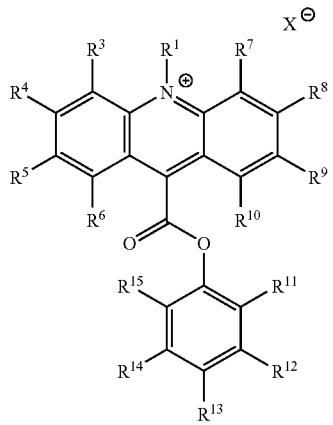

II

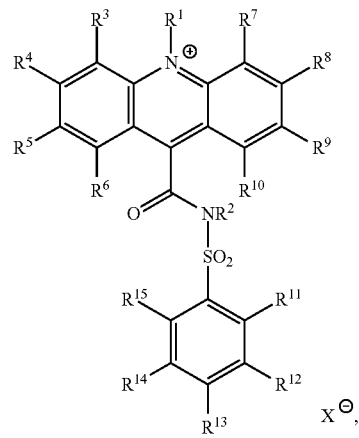

I wherein $R^1$ is an alkyl, alkenyl, alkynyl, aryl or aralkyl, sulfoalkyl, carboxyalkyl and oxoalkyl, and;

wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present, $X^\ominus$ is an anion.

2. The method of claim 1, wherein the test sample is non-biological forensic sample, stool, whole blood, serum, plasma, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil or a blood substitute.

3. The method of claim 1, wherein the basic solution is a solution having a pH of at least about 10.

4. The method of claim 1, wherein the indicator solution further comprises at least one surfactant.

5. The method of claim 1, further comprising measuring the amount of hemoglobin in the test sample by relating the amount of light generated in the test sample by comparison to a standard curve for hemoglobin or to a reference standard.

6. The method of claim 5, wherein the standard curve is generated from solutions of hemoglobin of a known concentration.

7. A method of diagnosing a subject suffering from a genetic disorder relating to hemoglobin metabolism, the method consisting essentially of the steps of:
a) adding at least one basic solution to a test sample obtained from a subject suspected of suffering from a genetic disorder relating to hemoglobin metabolism;
b) adding an indicator solution to the test sample to generate a light signal, wherein the indicator solution comprises at least one acridinium compound,
wherein steps a) and b) can be performed in any order;
c) quantifying the increased light generated to detect the hemoglobin in the test sample; and wherein the light generated is proportional to the amount of hemoglobin in the test sample; and
wherein the at least one acridinium compound comprises an acridinium-9-carboxamide or an acridinium-9-carboxylate aryl ester,
wherein the acridinium-9-carboxamide has a structure according to formula I:

wherein $R^1$ and $R^2$ are each independently selected from the group consisting of: alkyl, alkenyl, alkynyl, aryl or aralkyl, sulfoalkyl, carboxyalkyl and oxoalkyl, and;
wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present $X^\ominus$ is an anion, and
wherein acridinium-9-carboxylate aryl ester has a structure according to formula II:

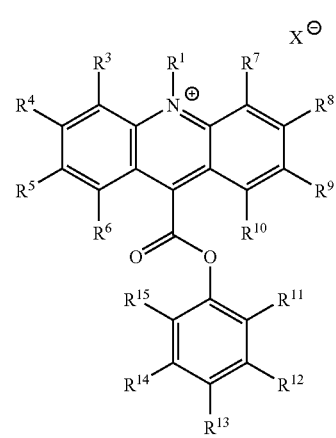

II wherein $R^1$ is an alkyl, alkenyl, alkynyl, aryl or aralkyl, sulfoalkyl, carboxyalkyl and oxoalkyl, and;
wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present $X^\ominus$ is an anion; and
d) determining the concentration of hemoglobin in the test sample based on the amount of light quantified in step c); and
e) comparing the concentration of hemoglobin in step (d) with a predetermined level, wherein if the concentration of hemoglobin determined in step (d) is lower or higher than the predetermined level, then a determination is made that the subject is suffering from a genetic disorder relating to hemoglobin metabolism.

8. The method of claim 7, wherein the test sample is serum, plasma, whole blood, red blood cells or umbilical cord blood.

9. The method of claim 7, wherein the basic solution is a solution having a pH of at least about 10.

10. The method of claim 7, wherein the indicator solution further comprises at least one surfactant.

11. The method of claim 7, further comprising measuring the amount of hemoglobin in the test sample by quantifying the amount of light generated in the test sample by comparison to a standard curve for hemoglobin or to a reference standard.

12. The method of claim 11, wherein the standard curve is generated from solutions of hemoglobin of a known concentration.

13. The method of claim 7, wherein the genetic disorder relating to hemoglobin metabolism is anemia or β-thalassemia.

14. A method of determining the eligibility of a subject to be a blood donor, the method consisting essentially of the steps of:
a) adding at least one basic solution to a test sample obtained from a subject;
b) adding an indicator solution to the test sample to generate a light signal,
wherein the indicator solution comprises at least one acridinium compound, wherein steps a) and b) can be performed in any order;
c) quantifying the increased light generated to detect the hemoglobin in the test sample; wherein the light generated is proportional to the amount of hemoglobin in the test sample; and
wherein the at least one acridinium compound comprises an acridinium-9-carboxamide or an acridinium-9-carboxylate aryl ester,
wherein the acridinium-9-carboxamide has a structure according to formula I:

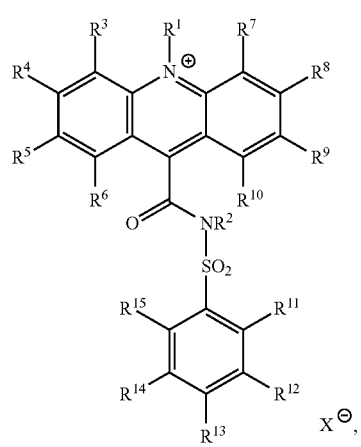

wherein $R^1$ and $R^2$ are each independently selected from the group consisting of: alkyl, alkenyl, alkynyl, aryl or aralkyl, sulfoalkyl, carboxyalkyl and oxoalkyl, and;
wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present, $X^\ominus$ is an anion, and wherein acridinium-9-carboxylate aryl ester has a structure according to formula II:

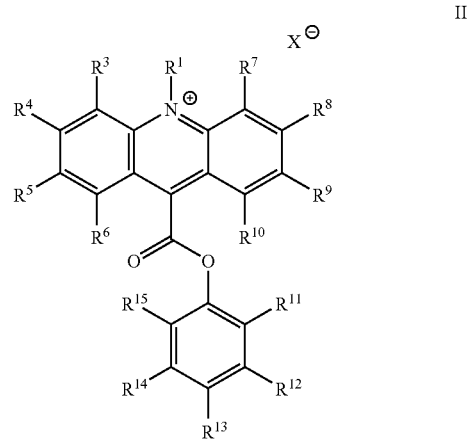

wherein $R^1$ is an alkyl, alkenyl, alkynyl, aryl or aralkyl, sulfoalkyl, carboxyalkyl and oxoalkyl, and;
wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present, $X^\ominus$ is an anion; and
d) determining the concentration of hemoglobin in the test sample based on the amount of light quantified in step c); and
e) comparing the concentration of hemoglobin in step (d) with a predetermined level, wherein if the concentration of hemoglobin determined in step (d) is lower or higher than the predetermined level, then a determination is made that the subject is not eligible to be a blood donor.

15. The method of claim 14, wherein the test sample is whole blood.

16. The method of claim 14, wherein the basic solution is a solution having a pH of at least about 10.

17. The method of claim 14, wherein the indicator solution further comprises at least one surfactant.

18. The method of claim 14, further comprising measuring the amount of hemoglobin in the test sample by quantifying the amount of light generated in the test sample by comparison to a standard curve for hemoglobin or to a reference standard.

19. The method of claim 18, wherein the standard curve is generated from solutions of hemoglobin of a known concentration.

20. A method of determining the age of a stored blood sample, the method consisting essentially of the steps of:
a) adding at least one basic solution to a blood sample;
b) adding an indicator solution to the blood sample to generate a light signal, wherein the indicator solution comprises at least one acridinium compound,
wherein steps a) and b) can be performed in any order;
c) quantifying the increased light generated to detect the hemoglobin in the blood sample; wherein the light generated is proportional to the amount of hemoglobin in the test sample; and
wherein the at least one acridinium compound comprises an acridinium-9-carboxamide or an acridinium-9-carboxylate aryl ester, wherein the acridinium-9-carboxamide has a structure according to formula I:

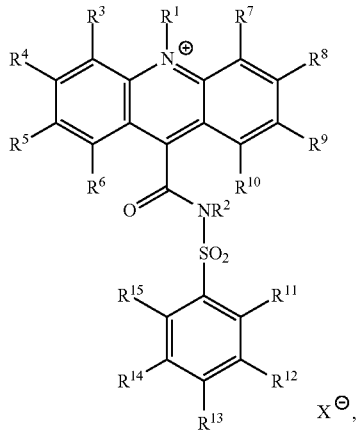

wherein $R^1$ and $R^2$ are each independently selected from the group consisting of: alkyl, alkenyl, alkynyl, aryl or aralkyl, sulfoalkyl, carboxyalkyl and oxoalkyl, and;

wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present, $X^\ominus$ is an anion, and wherein acridinium-9-carboxylate aryl ester has a structure according to formula II:

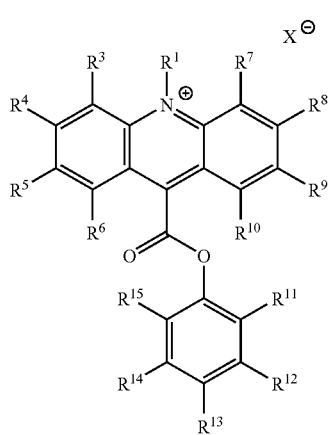

wherein $R^1$ is an alkyl, alkenyl, alkynyl, aryl or aralkyl, sulfoalkyl, carboxyalkyl and oxoalkyl, and;

wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present $X^\ominus$ is an anion; and d) determining the concentration of hemoglobin in the blood sample based on the amount of light quantified in step c); and e) comparing the concentration of hemoglobin in step (d) with at least one predetermined level, wherein if the concentration of hemoglobin determined in step (d) is lower than the predetermined level, then the plasma sample is determined to be an older blood sample.

21. The method of claim 20, wherein the blood sample is whole blood, serum, plasma, platelets, red blood cells or umbilical cord blood.

22. The method of claim 20, wherein the basic solution is a solution having a pH of at least about 10.

23. The method of claim 20, wherein the indicator solution further comprises at least one surfactant.

24. The method of claim 20, further comprising measuring the amount of hemoglobin in the blood sample by quantifying the amount of light generated in the blood sample by comparison to a standard curve for hemoglobin or to a reference standard.

25. The method of claim 24, wherein the standard curve is generated from solutions of hemoglobin of a known concentration.

26. A method of identifying a hemolyzed serum or plasma sample, the method consisting essentially of the steps of:
   a) adding at least one basic solution to a serum or plasma sample;
   b) adding an indicator solution to the serum or plasma sample to generate a light signal, wherein the indicator solution comprises at least one acridinium compound, wherein steps a) and b) can be performed in any order;
   c) quantifying the increased light generated to detect the hemoglobin in the serum or plasma sample; wherein the light generated is proportional to the amount of hemoglobin in the test sample; and
   wherein the at least one acridinium compound comprises an acridinium-9-carboxamide or an acridinium-9-carboxylate aryl ester, wherein the acridinium-9-carboxamide has a structure according to formula I:

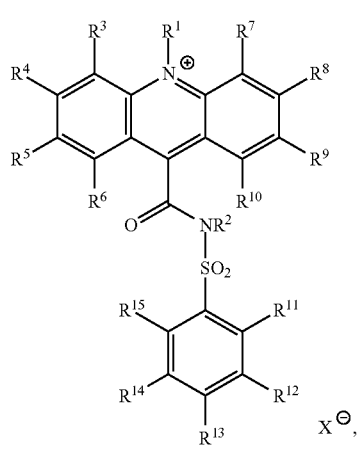

wherein $R^1$ and $R^2$ are each independently selected from the group consisting of: alkyl, alkenyl, alkynyl, aryl or aralkyl, sulfoalkyl, carboxyalkyl and oxoalkyl, and;

wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present, $X^\ominus$ is an anion, and wherein acridinium-9-carboxylate aryl ester has a structure according to formula II:

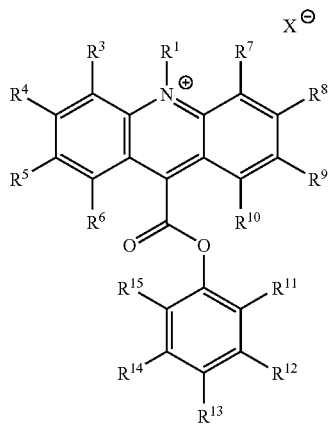

II wherein $R^1$ is an alkyl, alkenyl, alkynyl, aryl or aralkyl, sulfoalkyl, carboxyalkyl and oxoalkyl, and;

wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxylalkyl and oxoalkyl; and optionally, if present, $X^{\ominus}$ is an anion; and d) determining the concentration of hemoglobin in the serum or plasma sample based on the amount of light quantified in step c); and e) comparing the concentration of hemoglobin in step (d) with a predetermined level, wherein if the concentration of hemoglobin determined in step (d) is the same as or higher than the predetermined level, then the serum or plasma sample is determined to be hemolyzed and further wherein if the concentration of hemoglobin determined in step (d) is lower than the predetermined level, then the serum or plasma sample is determined not to be hemolyzed.

27. The method of claim 26, wherein the basic solution is a solution having a pH of at least about 10.

28. The method of claim 26, wherein the indicator solution further comprises at least one surfactant.

29. The method of claim 26, further comprising measuring the amount of hemoglobin in the serum or plasma sample by quantifying the amount of light generated in the serum or plasma sample by comparison to a standard curve for hemoglobin or to a reference standard.

30. The method of claim 29, wherein the standard curve is generated from solutions of hemoglobin of a known concentration.

* * * * *